(12) United States Patent
Ito et al.

(10) Patent No.: US 9,171,677 B2
(45) Date of Patent: Oct. 27, 2015

(54) IONIC LIQUID AND POWER STORAGE DEVICE INCLUDING THE SAME

(71) Applicant: SEMICONDUCTOR ENERGY LABORATORY CO., LTD., Atsugi-shi, Kanagawa-ken (JP)

(72) Inventors: Kyosuke Ito, Kanagawa (JP); Toru Itakura, Kanagawa (JP)

(73) Assignee: Semiconductor Energy Laboratory Co., Ltd., Kanagawa-ken (JP)

( * ) Notice: Subject to any disclaimer, the term of this patent is extended or adjusted under 35 U.S.C. 154(b) by 0 days.

(21) Appl. No.: 14/600,135

(22) Filed: Jan. 20, 2015

(65) Prior Publication Data

US 2015/0132665 A1    May 14, 2015

Related U.S. Application Data

(63) Continuation of application No. 13/479,582, filed on May 24, 2012, now Pat. No. 8,951,664.

(30) Foreign Application Priority Data

Jun. 3, 2011 (JP) ................................. 2011-125116

(51) Int. Cl.
*H01M 6/04* (2006.01)
*H01G 11/06* (2013.01)
(Continued)

(52) U.S. Cl.
CPC .............. *H01G 11/06* (2013.01); *C07C 309/06* (2013.01); *C07C 311/48* (2013.01);
(Continued)

(58) Field of Classification Search
CPC .................. H01M 2300/00; H01M 2300/0017
See application file for complete search history.

(56) References Cited

U.S. PATENT DOCUMENTS

| 5,202,042 A | 4/1993 | Tsuji et al. |
| 7,297,289 B2 | 11/2007 | Sato et al. |

(Continued)

FOREIGN PATENT DOCUMENTS

| CN | 001802362 A | 7/2006 |
| CN | 101103009 A | 1/2008 |

(Continued)

OTHER PUBLICATIONS

Sakaebe.H et al., "N-Methyl-N-propylpiperidinium bis(trifluoromethanesulfonyl)imide (PP13-TFSI)—novel electrolyte base for Li battery", Electrochemistry Communications, Jul. 1, 2003, vol. 5, No. 7, pp. 594-598.

(Continued)

*Primary Examiner* — Jane Rhee
(74) *Attorney, Agent, or Firm* — Nixon Peabody LLP; Jeffrey L. Costellia

(57) ABSTRACT

An ionic liquid having high electrochemical stability and a low melting point. An ionic liquid represented by the following general formula (G0) is provided.

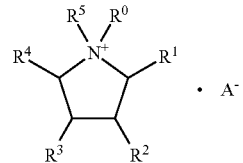

(G0)

In the general formula (G0), $R^0$ to $R^5$ are individually any of an alkyl group having 1 to 20 carbon atoms, a methoxy group, a methoxymethyl group, a methoxyethyl group, and a hydrogen atom, and $A^-$ is a univalent imide-based anion, a univalent methide-based anion, a perfluoroalkyl sulfonic acid anion, tetrafluoroborate, or hexafluorophosphate.

17 Claims, 17 Drawing Sheets

(51) Int. Cl.
  *C07D 207/06* (2006.01)
  *H01M 10/052* (2010.01)
  *H01M 10/0569* (2010.01)
  *H01G 11/62* (2013.01)
  *C07C 309/06* (2006.01)
  *C07C 311/48* (2006.01)
  *H01G 11/52* (2013.01)
  *H01G 11/60* (2013.01)
  *H01M 10/0525* (2010.01)

(52) U.S. Cl.
  CPC .............. *C07D 207/06* (2013.01); *H01G 11/52* (2013.01); *H01G 11/60* (2013.01); *H01G 11/62* (2013.01); *H01M 10/052* (2013.01); *H01M 10/0525* (2013.01); *H01M 10/0569* (2013.01); *H01M 2220/20* (2013.01); *H01M 2220/30* (2013.01); *H01M 2300/0017* (2013.01); *H01M 2300/0045* (2013.01); *Y02E 60/122* (2013.01); *Y02E 60/13* (2013.01); *Y02T 10/7011* (2013.01); *Y02T 10/7022* (2013.01)

(56) References Cited

U.S. PATENT DOCUMENTS

| | | |
|---|---|---|
| 7,834,197 B2 | 11/2010 | Nishida et al. |
| 7,875,732 B2 | 1/2011 | Nishida et al. |
| 8,088,917 B2 | 1/2012 | Forsyth et al. |
| 8,258,088 B2 | 9/2012 | Bodesheim et al. |
| 8,366,956 B2 | 2/2013 | Nishida et al. |
| 8,686,134 B2 | 4/2014 | Forsyth et al. |
| 8,747,690 B2 | 6/2014 | Nishida et al. |
| 8,794,469 B2 | 8/2014 | Bratsch |
| 8,795,544 B2 | 8/2014 | Ito et al. |
| 8,852,689 B2 | 10/2014 | Srinivas et al. |
| 2005/0106440 A1* | 5/2005 | Komiya ........................ 429/33 |
| 2007/0099079 A1 | 5/2007 | Matsumoto et al. |
| 2007/0099090 A1 | 5/2007 | Oh et al. |
| 2007/0235696 A1 | 10/2007 | Burrell et al. |
| 2008/0084158 A1 | 4/2008 | Shao et al. |
| 2008/0296531 A1 | 12/2008 | Whiston et al. |
| 2009/0045373 A1 | 2/2009 | Hammami et al. |
| 2010/0178555 A1 | 7/2010 | Best |
| 2010/0209784 A1 | 8/2010 | Yamazaki et al. |
| 2010/0227228 A1 | 9/2010 | Yamazaki et al. |
| 2010/0273063 A1 | 10/2010 | Wallace et al. |
| 2011/0020706 A1 | 1/2011 | Nesper |
| 2011/0070486 A1 | 3/2011 | Matsumoto et al. |
| 2011/0217544 A1 | 9/2011 | Young et al. |
| 2011/0281070 A1 | 11/2011 | Mittal et al. |
| 2011/0294005 A1 | 12/2011 | Kuriki et al. |
| 2012/0002349 A1 | 1/2012 | Ito et al. |
| 2012/0021279 A1 | 1/2012 | Le Bideau et al. |
| 2012/0045692 A1 | 2/2012 | Takemura et al. |
| 2012/0088151 A1 | 4/2012 | Yamazaki et al. |
| 2012/0088156 A1 | 4/2012 | Nomoto et al. |
| 2012/0152949 A1 | 6/2012 | Bratsch |
| 2012/0328960 A1 | 12/2012 | Ito et al. |
| 2013/0164609 A1 | 6/2013 | Ito et al. |
| 2013/0164610 A1 | 6/2013 | Itakura et al. |
| 2013/0224576 A1 | 8/2013 | Rosciano et al. |
| 2014/0041905 A1 | 2/2014 | Srinivas et al. |
| 2014/0299359 A1 | 10/2014 | Mittal et al. |
| 2014/0342245 A1 | 11/2014 | Ito et al. |

FOREIGN PATENT DOCUMENTS

| | | |
|---|---|---|
| CN | 101679899 A | 3/2010 |
| CN | 101821892 A | 9/2010 |
| CN | 101910263 A | 12/2010 |
| CN | 103250297 A | 8/2013 |
| EP | 0281994 A | 9/1988 |
| EP | 1642894 A | 4/2006 |
| EP | 1837333 A | 9/2007 |
| EP | 2172463 A | 4/2010 |
| EP | 2202826 A | 6/2010 |
| JP | 62-216171 A | 9/1987 |
| JP | 63-219116 A | 9/1988 |
| JP | 2002-313414 A | 10/2002 |
| JP | 2003-331918 A | 11/2003 |
| JP | 2005-139100 A | 6/2005 |
| JP | 2005-225843 A | 8/2005 |
| JP | 2005-251510 A | 9/2005 |
| JP | 2007-051219 A | 3/2007 |
| JP | 2008-084664 A | 4/2008 |
| JP | 2009-138254 A | 6/2009 |
| JP | 2012-033477 A | 2/2012 |
| WO | WO-2007/104144 | 9/2007 |
| WO | WO-2008/150842 | 12/2008 |
| WO | WO-2008/150867 | 12/2008 |
| WO | WO-2009/003224 | 1/2009 |
| WO | WO-2010/022353 | 2/2010 |
| WO | WO-2010/095082 | 8/2010 |
| WO | WO-2011/026993 | 3/2011 |
| WO | WO-2011/106730 | 9/2011 |
| WO | WO-2012/049780 | 4/2012 |

OTHER PUBLICATIONS

Matsumoto.H et al., "Fast cycling of Li/LiCoO2 cell with low-viscosity ionic liquids based on bis(fluorosulfonyl)imide [FSI]", Journal of Power Sources, Mar. 22, 2006, vol. 160, No. 2, pp. 1308-1313.

Macfarlane.D et al., "Pyrrolidinium Imides: A New Family of Molten Salts and Conductive Plastic Crystal Phases", J. Phys. Chem. B (Journal of Physical Chemistry B), Feb. 2, 1999, vol. 103, No. 20, pp. 4164-4170.

Mizuhata.M et al., "Thermophysical Properties of Binary Aliphatic Quaternary Ammonium Ionic Liquids: TMPAFSAxTFSA1-x", ECS Transactions, 2010, vol. 25, No. 39, pp. 3-12, The Electrochemical Society.

Chinese Office Action (Application No. 201210174566.7) Dated Mar. 9, 2015.

Suzuoki et al., "Stereospecific polymerization of DL-alanine NCA by basic quaternary ammonium compound", Japanese Journal of Polymer Science and Technology (Kobunshi Ronbunshu), Nov. 1974, vol. 31, No. 11, pp. 708-714.

Brown.D et al., "Diastereomeric Quaternary Salts from Cyclisation of αω-Dibromides with Secondary Amines", Journal of the Chemical Society. B. Physical Organic Chemistry, 1969, vol. 5, pp. 567-569, 572.

Mckenna.J at al., "Stereoisomeric Pairs of Cyclic Quaternary Ammonium Salts. Part IV. Interconversion of N-Benzyl-N-Methyl Quaternary Iodides in Hot Chloroform, and General Theoretical Discussion of Reactions Involving a Change Between Co-ordination Nos. 3 and 4 at a Six-ring Atom", J. Chem. Soc. (Journal of the Chemical Society), 1965, pp. 1733-1740.

* cited by examiner

330

IONIC LIQUID AND POWER STORAGE DEVICE INCLUDING THE SAME

BACKGROUND OF THE INVENTION

1. Field of the Invention

The present invention relates to an ionic liquid and a power storage device including the ionic liquid.

2. Description of the Related Art

Owing to the increase in demand for portable electronic devices such as a mobile phone and a laptop personal computer and the development of electric vehicles (EVs), the demand for power storage devices such as an electric double layer capacitor, a lithium-ion secondary battery, and a lithium-ion capacitor has been significantly increasing in recent years. For the power storage devices, high capacity, high performance, safety in various operating environments, and the like are required.

To satisfy the above requirements, electrolyte solutions for power storage devices have been actively developed. Cyclic carbonates are used for electrolyte solutions for power storage devices. In particular, ethylene carbonate is often used because of its high dielectric constant and high ionic conductivity.

However, not only an ethylene carbonate but also many organic solvents have volatility and a low flash point. For this reason, in the case where an organic solvent is used for an electrolyte solution of a power storage device, the temperature inside a lithium-ion secondary battery might rise due to a short circuit, overcharge, or the like and the lithium-ion secondary battery might burst or catch fire.

In consideration of the risks, use of an ionic liquid, which is nonvolatile and flame-retardant, for an electrolyte solution of a power storage device has been studied. An ionic liquid is also referred to as ambient temperature molten salt, which is a salt formed by combination of cations and anions. Examples of the ionic liquid include an ionic liquid including quaternary ammonium-based cations and an ionic liquid including imidazolium-based cations (see Patent Document 1 and Non-Patent Document 1).

REFERENCE

Patent Document

[Patent Document 1] Japanese Published Patent Application No. 2003-331918

Non-Patent Document

Hajime Matsumoto, et al., Fast cycling of Li/LiCoO$_2$ cell with low-viscosity ionic liquids based on bis(fluorosulfonyl) imide [FSI]$^-$, Journal of Power Sources 160, 2006, pp. 1308-1313

SUMMARY OF THE INVENTION

When an ionic liquid is used for an electrolyte solution of a power storage device, the ionic liquid needs to have a wide potential window and high electrochemical stability. Furthermore, the operating temperature of a power storage device ranges from −30° C. to 70° C. in many cases. In order to use the power storage device in various environments, particularly in a low-temperature environment, the ionic liquid preferably has a low melting point.

Patent Document 1 discloses an ionic liquid including quaternary ammonium-based cations which has a melting point of approximately 10° C. When the power storage device including such an ionic liquid is used in a low-temperature environment, there is a possibility that the ionic liquid solidifies and the resistance of the ionic liquid increases. In addition, a problem in which the range of operating temperature of the power storage device is narrowed occurs when it is difficult to use the power storage device in a low-temperature environment.

Furthermore, as described in Non-Patent Document 1, an ionic liquid including imidazolium-based cations has a narrower potential window and thus lower electrochemical stability than an ionic liquid including quaternary ammonium-based cations. Therefore, the ionic liquid including imidazolium-based cations is unstable to a positive-electrode material and a negative-electrode material; accordingly, the reliability of the power storage device might be decreased.

In view of the above problems, an object of an embodiment of the present invention is to provide an ionic liquid having high electrochemical stability and a low melting point. Another object is to provide a power storage device an electrolyte solution of which includes the ionic liquid.

An embodiment of the present invention is an ionic liquid including a cyclic quaternary ammonium cation and a univalent anion. The ionic liquid is represented by the following general formula (G0).

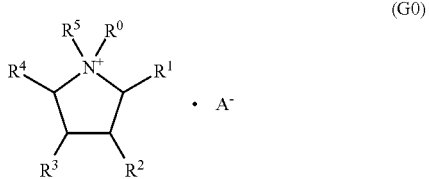

(G0)

In the general formula (G0), $R^0$ to $R^5$ are individually any of an alkyl group having 1 to 20 carbon atoms, a methoxy group, a methoxymethyl group, a methoxyethyl group, and a hydrogen atom, and A$^-$ is a univalent imide-based anion, a univalent methide-based anion, a perfluoroalkyl sulfonic acid anion, tetrafluoroborate (BF$_4^-$), or hexafluorophosphate (PF$_6^-$).

Another embodiment of the present invention is an ionic liquid including a cyclic quaternary ammonium cation and a univalent anion. The ionic liquid is represented by the following general formula (G1).

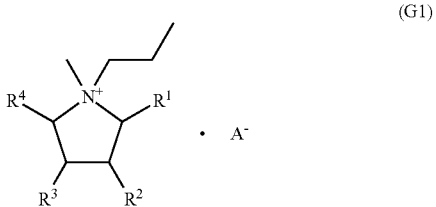

(G1)

In the general formula (G1), one or two of $R^1$ to $R^4$ are any of an alkyl group having 1 to 20 carbon atoms, a methoxy group, a methoxymethyl group, and a methoxyethyl group. The other two or three of $R^1$ to $R^4$ are hydrogen atoms, and A$^-$ is a univalent imide-based anion, a univalent methide-based anion, a perfluoroalkyl sulfonic acid anion, BF$_4^-$, or PF$_6^-$.

In the general formula (G1), it is preferable that one or two of $R^1$ to $R^4$ be each an alkyl group having 1 to 4 carbon atoms.

Another embodiment of the present invention is an ionic liquid including a cyclic quaternary ammonium cation and a univalent anion. The ionic liquid is represented by the following general formula (G2).

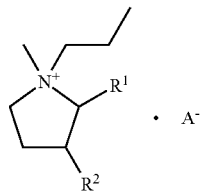

(G2)

In the general formula (G2), $R^1$ and $R^2$ are individually any of an alkyl group having 1 to 20 carbon atoms, a methoxy group, a methoxymethyl group, and a methoxyethyl group, and $A^-$ is a univalent imide-based anion, a univalent methide-based anion, a perfluoroalkyl sulfonic acid anion, $BF_4^-$, or $PF_6^-$.

In the general formula (G2), it is preferable that $R^1$ and $R^2$ individually be an alkyl group having 1 to 4 carbon atoms.

Another embodiment of the present invention is an ionic liquid including a cyclic quaternary ammonium cation and a univalent anion. The ionic liquid is represented by the general formula (G3).

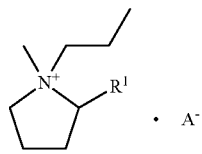

(G3)

In the general formula (G3), $A^-$ is a univalent imide-based anion, a univalent methide-based anion, a perfluoroalkyl sulfonic acid anion, $BF_4^-$, or $PF_6^-$.

Another embodiment of the present invention is an ionic liquid including a cyclic quaternary ammonium cation and a univalent anion. The ionic liquid is represented by the general formula (G4).

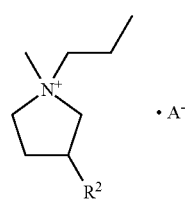

(G4)

In the general formula (G4), $A^-$ is a univalent imide-based anion, a univalent methide-based anion, a perfluoroalkyl sulfonic acid anion, $BF_4^-$, or $PF_6^-$.

Another embodiment of the present invention is an ionic liquid including a cyclic quaternary ammonium cation and a univalent anion. The ionic liquid is represented by the general formula (G5).

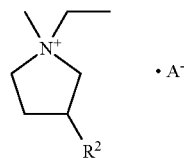

(G5)

In the general formula (G5), $A^-$ is a univalent imide-based anion, a univalent methide-based anion, a perfluoroalkyl sulfonic acid anion, $BF_4^-$, or $PF_6^-$.

In the general formulae (G0) to (G5), $A^-$ is preferably any one of univalent anions selected from $(C_nF_{2n+1}SO_2)_2N^-$ (n=0 to 4), $(C_mF_{2m+1}SO_3)^-$ (m=0 to 4), and $CF_2(CF_2SO_2)_2N^-$.

Another embodiment of the present invention is a power storage device including a positive electrode, a negative electrode, a separator, and an electrolyte solution. The electrolyte solution includes an ionic liquid represented by any of the general formulae (G0) to (G5).

Another embodiment of the present invention is a power storage device including a positive electrode, a negative electrode, a separator, and an electrolyte solution. The electrolyte solution includes an ionic liquid represented by any of the general formulae (G0) to (G5) and electrolyte salt including a lithium ion.

Note that the power storage device in this specification indicates all elements and devices which have the function of storing power. For example, a lithium-ion secondary battery, a lithium-ion capacitor, and an electric double layer capacitor are included in the category of the power storage device.

According to an embodiment of the present invention, an ionic liquid having high electrochemical stability and a low melting point can be provided. Further, a power storage device an electrolyte solution of which includes an ionic liquid according to an embodiment of the present invention can be provided.

BRIEF DESCRIPTION OF THE DRAWINGS

In the accompanying drawings.

DETAILED DESCRIPTION OF THE INVENTION

Figure 1B:
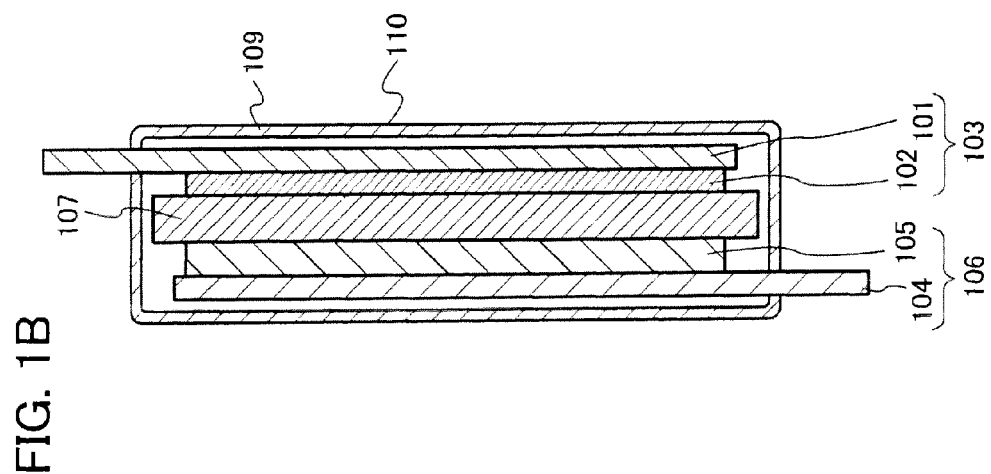
FIGS. 1A and 1B are cross-sectional views illustrating power storage devices.

Hereinafter, embodiments of the present invention will be described in detail with reference to the accompanying drawings. Note that the present invention is not limited to the description below, and it is easily understood by those skilled in the art that a variety of changes and modifications can be made without departing from the spirit and scope of the present invention. Therefore, the present invention is not construed as being limited to the description of the embodiments and examples given below.

Embodiment 1

An embodiment of the present invention is an ionic liquid including a cyclic quaternary ammonium cation and a univalent anion. The ionic liquid is represented by the following general formula (G0).

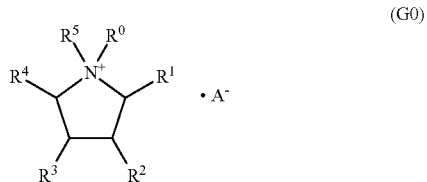

(G0)

In the general formula (G0), $R^0$ to $R^5$ are individually any of an alkyl group having 1 to 20 carbon atoms, a methoxy group, a methoxymethyl group, a methoxyethyl group, and a hydrogen atom, and $A^-$ is a univalent imide-based anion, a univalent methide-based anion, a perfluoroalkyl sulfonic acid anion, $BF_4^-$, or $PF_6^-$.

Another embodiment of the present invention is an ionic liquid including a cyclic quaternary ammonium cation and a univalent anion. The ionic liquid is represented by the following general formula (G1).

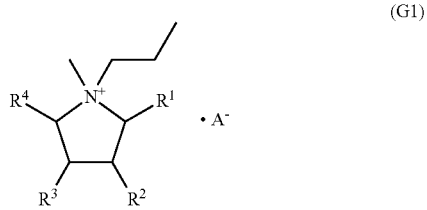

(G1)

In the general formula (G1), one or two of $R^1$ to $R^4$ are any of an alkyl group having 1 to 20 carbon atoms, a methoxy group, a methoxymethyl group, and a methoxyethyl group. The other two or three of $R^1$ to $R^4$ are hydrogen atoms, and $A^-$ is a univalent imide-based anion, a univalent methide-based anion, a perfluoroalkyl sulfonic acid anion, $BF_4^-$, or $PF_6^-$.

In the general formula (G1), it is preferable that one or two of $R^1$ to $R^4$ be each alkyl group having 1 to 4 carbon atoms.

Another embodiment of the present invention is an ionic liquid including a cyclic quaternary ammonium cation and a univalent anion. The ionic liquid is represented by the following general formula (G2).

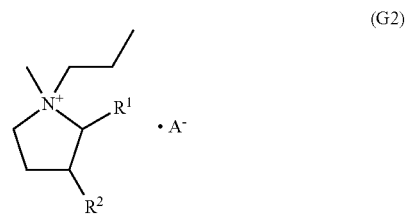

(G2)

In the general formula (G2), $R^1$ and $R^2$ are individually any of an alkyl group having 1 to 20 carbon atoms, a methoxy group, a methoxymethyl group, and a methoxyethyl group, and $A^-$ is a univalent imide-based anion, a univalent methide-based anion, a perfluoroalkyl sulfonic acid anion, $BF_4^-$, or $PF_6^-$.

In the general formula (G2), it is preferable that $R^1$ and $R^2$ individually be an alkyl group having 1 to 4 carbon atoms.

Another embodiment of the present invention is an ionic liquid including a cyclic quaternary ammonium cation and a univalent anion. The ionic liquid is represented by the following general formula (G3).

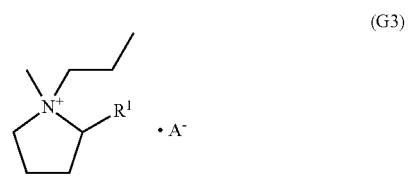

(G3)

In the general formula (G3), $A^-$ is a univalent imide-based anion, a univalent methide-based anion, a perfluoroalkyl sulfonic acid anion, $BF_4^-$, or $PF_6^-$.

Another embodiment of the present invention is an ionic liquid including a cyclic quaternary ammonium cation and a univalent anion. The ionic liquid is represented by the following general formula (G4).

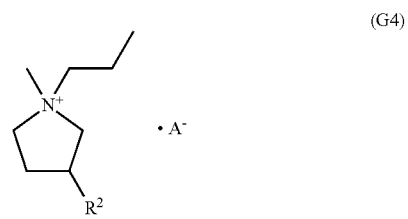

(G4)

In the general formula (G4), $A^-$ is a univalent imide-based anion, a univalent methide-based anion, a perfluoroalkyl sulfonic acid anion, $BF_4^-$, or $PF_6^-$.

Another embodiment of the present invention is an ionic liquid including a cyclic quaternary ammonium cation and a univalent anion. The ionic liquid is represented by the general formula (G5).

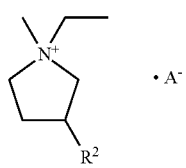

(G5)

In the general formula (G5), A⁻ is a univalent imide-based anion, a univalent methide-based anion, a perfluoroalkyl sulfonic acid anion, $BF_4^-$, or $PF_6^-$.

Specific examples of the cyclic quaternary ammonium cation include organic compounds represented by the structural formulae (100) to (117). Note that embodiments of the present invention are not limited thereto.

(100)

(101)

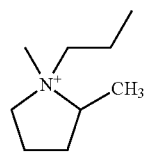

(102)

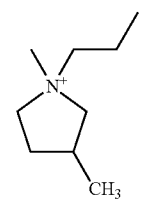

(103)

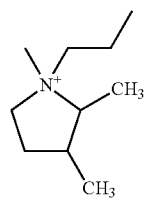

(104)

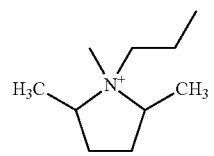

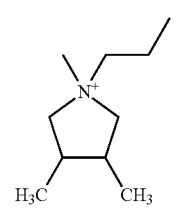

(105)

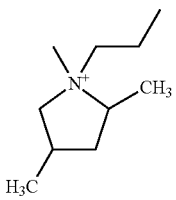

(106)

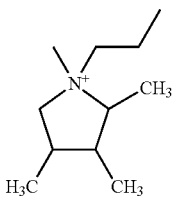

(107)

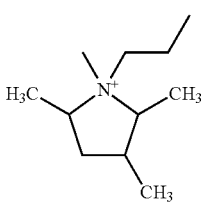

(108)

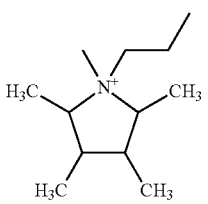

(109)

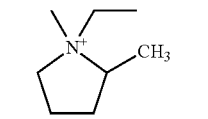

(110)

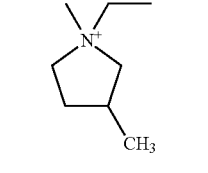

(111)

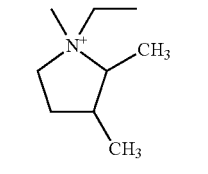

(112)

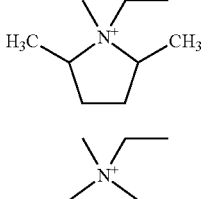

(113)

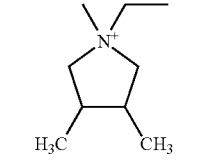

-continued (114)
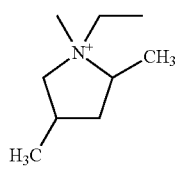

(115)
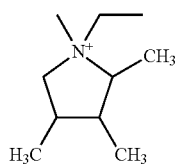

(116)
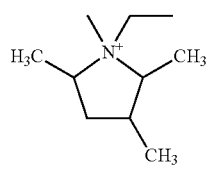

(117)
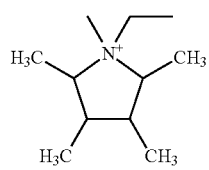

Here, calculation results of an improvement of the reduction resistance due to an electron donating substituent are shown.

As a cation included in an ionic liquid according to an embodiment of the present invention, 1,2-dimethyl-1-propylpyrrolidinium cation (abbreviation: 2mP13) represented by the structural formula (100). 1,3-dimethyl-1-propylpyrrolidinium cation (abbreviation: 3mP13) represented by the structural formula (101), and 1-ethyl-1,3-dimethylpyrrolidinium cation (abbreviation: 3mP12) represented by the structural formula (110) are shown below. As a cation included in a comparative ionic liquid, 1-methyl-1-propylpyrrolidinium cation (abbreviation: P13) represented by the structural formula (301), and 1-ethyl-3-methylimidazolium cation (abbreviation: EMI) represented by the structural formula (302) are shown below.

(100)
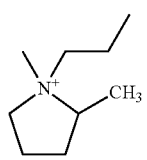

(101)
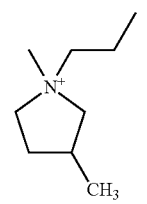

(110)
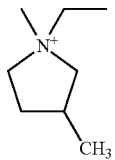

(301)
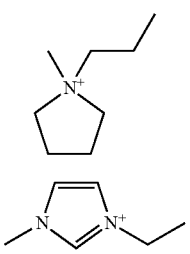

(302)
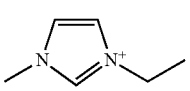

In the quantum chemistry computation, the optimal molecular structures in the singlet excited state of cations each included in an ionic liquid according to an embodiment of the present invention (structural formulae (100), (101), and (110)) and cations each included in the comparative ionic liquid (structural formulae (301) and (302)) are calculated by using density functional theory (DFT). In the DFT, the total energy is represented as the sum of potential energy, electrostatic energy between electrons, electronic kinetic energy, and exchange-correlation energy including all the complicated interactions between electrons. In the DFT, an exchange-correlation interaction is approximated by a functional (that is, a function of another function) of one electron potential represented in terms of electron density to enable high-speed and highly-accurate calculations. Here, B3LYP, which is a hybrid functional, is used to specify the weight of each parameter related to exchange-correlation energy. In addition, as a basis function, 6-311G (a basis function of a triple-split valence basis set using three contraction functions for each valence orbital) is applied to all the atoms. By the above basis function, for example, orbits of 1s to 3s are considered in the case of hydrogen atoms while orbits of 1s to 4s and 2p to 4p are considered in the case of carbon atoms. Furthermore, to improve calculation accuracy, the p function and the d function as polarization basis sets are added to hydrogen atoms and atoms other than hydrogen atoms, respectively.

Note that Gaussian 09 was used as a quantum chemistry computational program. The calculations were performed using a high performance computer (Altix ICE8400EX manufactured by SGI). The quantum chemistry computation was performed on the assumption that all of the cations represented by the structural formulae (100), (101), (110), (301), and (302) included in ionic liquids have the most stable structure and were in a vacuum.

Table 1 shows the lowest unoccupied molecular orbital levels (LUMO levels), which are calculated by the quantum chemistry computation, of three types of cations represented by the structural formulae (100), (101), and (110) included in ionic liquids. For comparison, Table 1 also shows the lowest unoccupied molecular orbital levels (LUMO levels) of two types of cations represented by the structural formulae (301) and (302) in ionic liquids.

TABLE 1

| | LUMO level [eV] |
|---|---|
| Structural formula (100) | −3.39 |
| Structural formula (101) | −3.47 |
| Structural formula (110) | −3.31 |
| Structural formula (301) | −3.50 |
| Structural formula (302) | −5.11 |

When an ionic liquid is used for an electrolyte solution of a power storage device, the reduction resistance of the ionic liquid depends on the electron acceptability of a cation in the ionic liquid from a negative electrode.

For example, when the LUMO level of a cation included in the ionic liquid is higher than a conduction band of a negative-electrode material, the ionic liquid including the cation is not reduced. The reduction resistance of the cation with respect to lithium can be relatively evaluated by comparing the LUMO level of the cation with the LUMO level of the EMI cation represented by the structural formula (302) having a reduction potential substantially equivalent to an oxidation-reduction potential of lithium that is a typical low potential negative electrode material. In other words, when a cation included in an ionic liquid according to an embodiment of the present invention has a higher LUMO level than at least an EMI cation represented by the structural formula (302), the ionic liquid according to the embodiment of the present invention has excellent reduction resistance.

As shown in Table 1, a P13 cation represented by the structural formula (301) has a LUMO level of −3.50 eV, while a 2mP13 cation represented by the structural formula (100), a 3mP13 cation represented by the structural formula (101), and a 3mP12 cation represented by the structural formula (110) each have a LUMO level higher than −3.50 eV. Therefore, the ionic liquids according to the embodiments of the present invention have excellent reduction resistance.

The above calculation results indicate that the reduction resistance of an ionic liquid is improved by introduction of an electron donating substituent to a cation of the ionic liquid.

In the general formulae (G0) to (G5), $A^-$ is preferably any one of univalent anions selected from $(C_nF_{2n+1}SO_2)_2N^-$ (n=0 to 4), $(C_mF_{2m+1}SO_3)^-$ (m=0 to 4), and $CF_2(CF_2SO_2)_2N^-$. Note that $A^-$ is not limited thereto and may be any anion as long as it pairs with a cyclic quaternary ammonium cation to form an ionic liquid.

The oxidation potential of the ionic liquid differs depending on types of anions. When any one of univalent anions selected from $(C_nF_{2n+1}SO_2)_2N^-$ (n=0 to 4), $(C_mF_{2m+1}SO_3)^-$ (m=0 to 4), and $CF_2(CF_2SO_2)_2N^-$ is used, the oxidation potential of the ionic liquid can be high due to mutual interaction with the above anion. This means that the oxidation resistance of the ionic liquid can be improved.

Next, a method for synthesizing an ionic liquid according to an embodiment of the present invention is described. A variety of reactions can be applied to the method for synthesizing the ionic liquid according to an embodiment of the present invention. For example, an ionic liquid represented by the general formula (G1) can be synthesized by a synthesis method described below. Note that the method for synthesizing the ionic liquid according to an embodiment of the present invention is not limited to the following synthesis methods.

<Method for Synthesizing Ionic Liquid Represented by General Formula (G1)>

Various types of reactions can be applied to the method for synthesizing an ionic liquid according an embodiment of the present invention. Here, an example is described referring to the synthesis scheme (S-1).

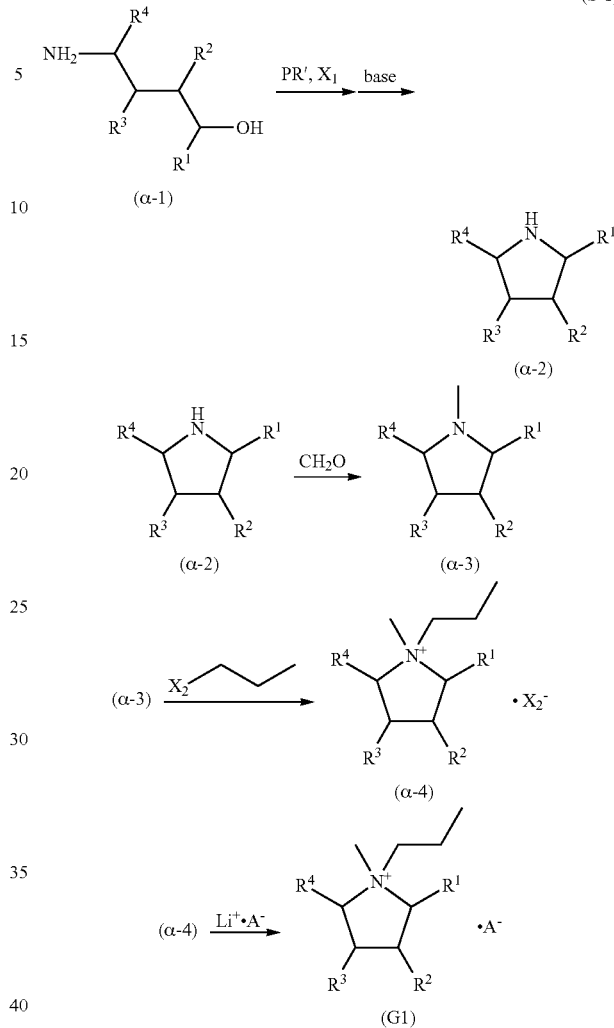

In the synthesis scheme (S-1), a reaction from the general formula (α-1) to the general formula (α-2) is a ring closure reaction of amino alcohol which passes through halogenation using trisubstituted phosphine such as trialkylphosphine and halogen source. PR' represents trisubstituted phosphine and $X_1$ represents halogen source. As the halogen source, carbon tetrachloride, carbon tetrabromide, iodine, or iodomethane can be used, for example. In the ionic liquid according to an embodiment of the present invention, triphenylphosphine is used as the trisubstituted phosphine and carbon tetrachloride is used as the halogen source.

In the above scheme (S-1), the reaction from the general formula (α-2) to the general formula (α-3) is alkylation of amine by an amine compound and a carbonyl compound in the presence of hydride. For example, excessive formic acid can be used as the hydride source. $CH_2O$ is used as the carbonyl compound in the ionic liquid according to an embodiment of the present invention.

In the above scheme (S-1), the reaction from the general formula (α-3) to the general formula (α-4) is alkylation by a tertiary amine compound and an alkyl halide compound, which synthesizes quaternary ammonium salt. As the alkyl halide compound, propane halide or bromoethane can be used. Further, $X_2$ represents halogen. The halogen is preferably bromine, more preferably iodine, in terms of high reactivity.

Through ion exchange between the quaternary ammonium salt represented by the general formula (α-4) and desired metal salt, the ionic liquid represented by the general formula (G1) can be obtained. As the metal salt, lithium metal salt can be used, for example.

<Method for Synthesizing Ionic Liquid Represented by General Formula (G4)>

Next, a method for synthesizing an ionic liquid according an embodiment of the present invention is described referring to the synthesis scheme (S-2).

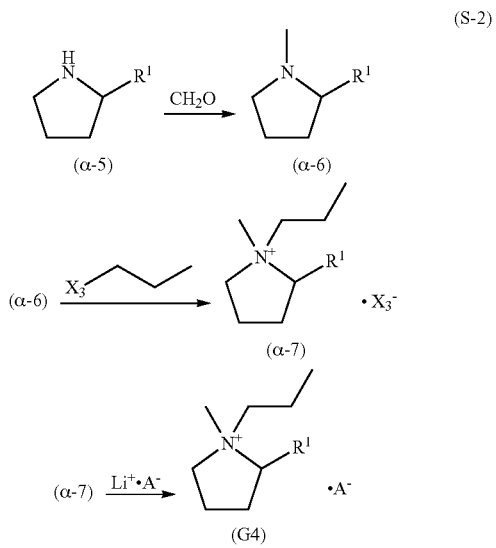

In the above scheme (S-2), the reaction from the general formula (α-5) to the general formula (α-6) is alkylation of amine by an amine compound and a carbonyl compound in the presence of hydride. For example, excessive formic acid can be used as the hydride source. $CH_2O$ is used as the carbonyl compound in the ionic liquid according to an embodiment of the present invention.

In the above scheme (S-2), the reaction from the general formula (α-6) to the general formula (α-7) is alkylation by a tertiary amine compound and an alkyl halide compound, which synthesizes quaternary ammonium salt. As the alkyl halide compound, propane halide or bromoethane can be used. Further, $X_3$ represents halogen. The halogen is preferably bromine, more preferably iodine, in terms of high reactivity.

Through ion exchange between the quaternary ammonium salt represented by the general formula (α-7) and desired metal salt, the ionic liquid represented by the general formula (G4) can be obtained. As the metal salt, lithium metal salt can be used, for example.

The ionic liquid according to the embodiment of the present invention has a wide potential window greater than or equal to 0.2 and less than or equal to 5.4, preferably greater than or equal to −0.1 and less than or equal to 5.8. That is, the ionic liquid according to the embodiment of the present invention has high electrochemical stability.

Furthermore, the melting point of the ionic liquid can be decreased by introduction of a substituent to the cyclic quaternary ammonium. For example, the melting point can be decreased by introduction of a methyl group to a pyrrolidine skeleton. The melting point of the ionic liquid according to the embodiment of the present invention can be less than or equal to −10° C., preferably less than or equal to −30° C. The reason for this decrease in melting point is that the symmetry of the cyclic quaternary ammonium molecule is broken by the introduction of a substituent to the cyclic quaternary ammonium.

This embodiment can be implemented in appropriate combination with any of the other embodiments.

Embodiment 2

In this embodiment, a power storage device in which the ionic liquid according to an embodiment of the present invention is used for an electrolyte solution is described with reference to FIGS. 1A and 1B, FIGS. 2A and 2B, FIGS. 3A and 3B, and FIG. 4.

The power storage device according to an embodiment of the present invention includes at least a positive electrode, a negative electrode, a separator, and an electrolyte solution. For example, an electrolyte solution used for a lithium-ion secondary battery or a lithium-ion capacitor includes a nonaqueous solvent and electrolyte salt. The ionic liquid according to an embodiment of the present invention can be used for the nonaqueous solvent in which the electrolyte salt dissolves. Alternatively, only the ionic liquid according to an embodiment of the present invention can be used for an electrolyte solution in an electric double layer capacitor without use of the electrolyte salt.

Figure 1A:
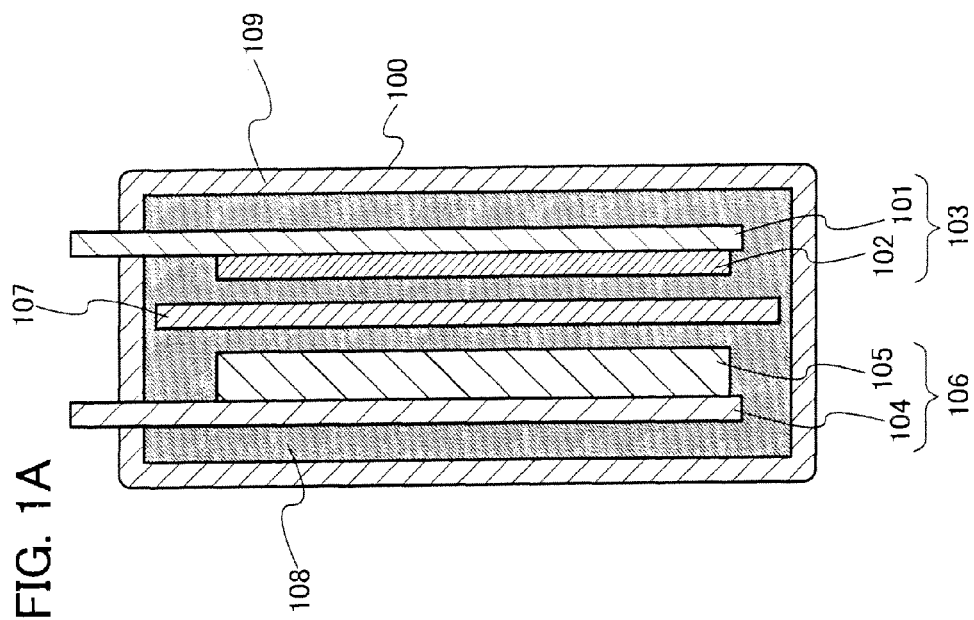

FIG. 1A illustrates a structure of a power storage device 100. The case where the power storage device 100 is a lithium-ion secondary battery is described below as an example.

The power storage device 100 illustrated in FIG. 1A includes a positive electrode 103 including a positive electrode current collector 101 and a positive electrode active material layer 102, a negative electrode 106 including a negative electrode current collector 104 and a negative electrode active material layer 105, a separator 107, an electrolyte solution 108, and a housing 109. The separator 107 is placed between the positive electrode 103 and the negative electrode 106 provided in the housing 109. The inside of the housing 109 is filled with the electrolyte solution 108.

For the positive electrode current collector 101, a conductive material can be used, for example, Examples of the conductive material include aluminum (Al), copper (Cu), nickel (Ni), and titanium (Ti). In addition, an alloy material including two or more of the above-mentioned conductive materials can be used for the positive electrode current collector 101. Examples of the alloy material include an Al—Ni alloy and an Al—Cu alloy. The positive electrode current collector 101 can have, for example, a foil shape, a plate shape, or a net shape as appropriate. Further, the positive electrode current collector 101 can be formed in such a manner that a conductive layer is formed over another formation substrate, and the conductive layer is separated from the formation substrate.

For the positive electrode active material layer 102, a material including ions to serve as carriers and a transition metal can be used, for example. As the material including ions to serve as carriers and a transition metal, a material represented by a general formula $A_hM_iPO_j$ (h>0, i>0, j>0) can be used, for example. Here, A represents, for example, an alkali metal such as lithium, sodium, or potassium; or an alkaline earth metal such as calcium, strontium, or barium; beryllium; or magnesium. M represents, for example, a transition metal such as iron, nickel, manganese, or cobalt. Examples of the material represented by the general formula $A_hM_iPO_j$ (h>0, i>0, j>0) include lithium iron phosphate and sodium iron phosphate. The material represented by A and the material represented by M may be selected from one or more of the above materials.

Alternatively, a material represented by the general formula $A_hM_tO_j$ (h>0, i>0, j>0) can be used. Here, A represents, for example, an alkali metal such as lithium, sodium, or potassium; an alkaline earth metal such as calcium, strontium, or barium; beryllium; or magnesium. M represents, for example, a transition metal such as iron, nickel, manganese, or cobalt. Examples of the material represented by the general formula $A_hM_tO_j$ (h>0, i>0, j>0) include lithium cobaltate, lithium manganate, and lithium nickelate. The material represented by A and the material represented by M may be selected from one or more of the above materials.

In the case where the power storage device 100 is a lithium-ion secondary battery, a material including lithium is preferably selected for the positive electrode active material layer 102. In other words, A in the above general formulae $A_hM_tPO_j$ (h>0, i>0, j>0) or $A_hM_tO_j$ (h>0, i>0, j>0) is preferably lithium.

Here, the term "active material" refers only to a material related to insertion and extraction of ions to serve as carriers. Note that in this specification and the like, not only the above-described material (material that is literally a "positive electrode active material") but also the above-described material including a conduction auxiliary agent, a binder, and/or the like is referred to as positive electrode active material layer 102 in some cases.

Note that the conduction auxiliary agent may be an electron-conductive material which does not cause chemical change in the power storage device. For example, a carbon-based material such as acetylene black, graphite, or carbon fiber; a metal material such as copper, nickel, aluminum, or silver; and powder, fiber, and the like of mixtures thereof are given.

As the binder, polysaccharides such as starch, carboxymethyl cellulose, hydroxypropyl cellulose, regenerated cellulose, and diacetyl cellulose; vinyl polymers such as polyvinyl chloride, polyethylene, polypropylene, polyvinyl alcohol, polyvinyl pyrrolidone, polytetrafluoroethylene, polyvinylidene difluoride, ethylene-propylene-diene monomer (EPDM) rubber, sulfonated EPDM rubber, styrene-butadiene rubber, butadiene rubber, and fluorine rubber; polyether such as polyethylene oxide; and the like are given.

For the negative electrode current collector 104, a conductive material can be used, for example. Examples of the conductive material include aluminum (Al), copper (Cu), nickel (Ni), and titanium (Ti). In addition, an alloy material including two or more of the above-mentioned conductive materials can be used for the negative electrode current collector 104. Examples of the alloy material include an Al—Ni alloy and an Al—Cu alloy. The negative electrode current collector 104 can have, for example, a foil shape, a plate shape, or a net shape as appropriate. Further, the negative electrode current collector 104 can be formed in such a manner that a conductive layer is formed over another formation substrate, and the conductive layer is separated from the formation substrate.

There is no particular limitation on the material for the negative electrode active material layer 105 as long as it is a material with which metal can be dissolved/precipitated or a material in/from which metal ions can be inserted/extracted. For the negative electrode active material layer 105, a lithium metal, a carbon-based material, silicon, a silicon alloy, or tin can be used, for example. As the carbon-based material in/from which a lithium ion can be inserted/extracted, a fine graphite powder, a graphite fiber, or graphite can be used, for example.

Note that the negative electrode active material layer 105 may be predoped with lithium. Predoping with lithium may be performed in such a manner that a lithium layer is formed on a surface of the negative electrode active material layer 105 by a sputtering method. Alternatively, a lithium foil is provided on the surface of the negative electrode active material layer 105, whereby the negative electrode active material layer 105 can be predoped with lithium.

The electrolyte solution 108 includes a nonaqueous solvent and electrolyte salt. For the nonaqueous solvent, one or more of the ionic liquids each according to an embodiment of the present invention can be used. Note that the nonaqueous solvent is not necessarily a single solvent of the ionic liquid according to an embodiment of the present invention. The nonaqueous solvent may be a mixed solvent in which any of the ionic liquids each according to an embodiment of the present invention and another ionic liquid are mixed.

As an electrolyte solution of a power storage device has a lower reduction potential and higher oxidation potential, that is, a wider oxidation-reduction potential window, the number of materials which can be selected for a positive electrode and a negative electrode can be increased. Further, as the electrolyte solution has a wider oxidation-reduction potential window, the electrolyte solution can be stable to the selected materials for the positive electrode and the negative electrode. With the use of the ionic liquid according to an embodiment of the present invention having a wide oxidation-reduction potential window for the electrolyte solution, the reliability of the lithium-ion secondary battery can be increased.

The electrolyte salt dissolved in the nonaqueous solvent may be electrolyte salt which includes ions to serve as carriers and corresponds with the positive electrode active material layer 102. The electrolyte salt may be electrolyte salt including an alkali metal ion, an alkaline earth metal ion, a beryllium ion, or a magnesium ion. Examples of the alkali metal ion include a lithium ion, a sodium ion, and a potassium ion. Examples of the alkaline earth metal ion include a calcium ion, a strontium ion, and a barium ion. In the case where a material including lithium is used for the positive electrode active material layer 102, electrolyte salt including a lithium ion (hereinafter also referred to as electrolyte salt including lithium) can be selected. In the case where a material including sodium is used for the positive electrode active material layer 102, electrolyte salt including sodium is preferably selected.

Examples of the electrolyte salt including lithium include lithium chloride (LiCl), lithium fluoride (LiF), lithium perchlorate ($LiClO_4$), lithium fluoroborate ($LiBF_4$), $LiAsF_6$, $LiPF_6$, and $Li(CF_3SO_2)_2N$.

As the separator 107, paper, nonwoven fabric, a glass fiber, a synthetic fiber such as nylon (polyimide), vinylon (a polyvinyl alcohol based fiber), polyester, acrylic, polyolefin, or polyurethane, or the like may be used. However, a material which does not dissolve in the electrolyte solution 108 should be selected.

As the separator 107, high-molecular compounds based on fluorine-based polymer, polyether such as polyethylene oxide and polypropylene oxide, polyolefin such as polyethylene and polypropylene, polyacrylonitrile, polyvinylidene chloride, polymethyl methacrylate, polymethylacrylate, polyvinyl alcohol, polymethacrylonitrile, polyvinyl acetate, polyvinylpyrrolidone, polyethyleneimine, polybutadiene, polystyrene, polyisoprene, and polyurethane, derivatives thereof, cellulose, paper, and nonwoven fabric can be used either alone or in combination.

For the housing 109, a laminate film, a polymer film, a metal film, a metal case, or a plastic case can be used either alone or in combination.

Next, a power storage device 110, which has a different structure from the power storage device 100 illustrated in FIG. 1A, is described with reference to FIG. 1B.

The power storage device 110 illustrated in FIG. 1B includes a positive electrode 103 including a positive electrode current collector 101 and a positive electrode active material layer 102, a negative electrode 106 including a negative electrode current collector 104 and a negative electrode active material layer 105, a separator 107, an electrolyte solution, and a housing 109, which is the same as the power storage device 100 illustrated in FIG. 1A. In the power storage device 110 illustrated in FIG. 1B, the separator 107, which is placed between the positive electrode 103 and the negative electrode 106 provided in the housing 109, is impregnated with the electrolyte solution.

Materials for the positive electrode current collector 101, the positive electrode active material layer 102, the negative electrode current collector 104, the negative electrode active material layer 105, and the housing 109 in the power storage device 110 can be the same as those in the power storage device 100.

In the power storage device 110, the separator 107 is preferably a porous film. As a material for the porous film, a glass fiber, a synthetic resin material, a ceramic material, or the like can be used. In addition, the electrolyte solution with which the separator 107 is impregnated can be the same as that in the power storage device 100.

Next, a method for manufacturing the power storage device 100 is described. The case where the power storage device 100 is a lithium-ion secondary battery is described below as an example.

First, the positive electrode active material layer 102 is formed over the positive electrode current collector 101, so that the positive electrode 103 is formed. The positive electrode active material layer 102 can be formed by a coating method or a sputtering method using the above-described material. In the case of employing a coating method for forming the positive electrode active material layer 102, a conduction auxiliary agent, a binder, etc. is mixed with a material including ions serving as carriers and a transition metal to form a paste, and the paste is applied onto the positive electrode current collector 101 and dried. In the case of forming the positive electrode active material layer 102 by a coating method, pressure forming may also be employed, if necessary.

Next, the negative electrode active material layer 105 is formed over the negative electrode current collector 104, so that the negative electrode 106 is formed. The negative electrode active material layer 105 can be formed by a coating method, a plasma CVD method, or a sputtering method using the above-described material. In the case where silicon is used for the negative electrode active material layer 105, a microcrystalline silicon film may be formed and then amorphous silicon may be removed from the microcrystalline silicon by etching. The removal of amorphous silicon from microcrystalline silicon, the surface area of the remaining microcrystalline silicon is increased. The microcrystalline silicon film may be formed by a plasma CVD method or a sputtering method. Alternatively, in the case where the negative electrode active material layer 105 is formed by a coating method, a conduction auxiliary agent, a binder, etc. is mixed with a material with which metal can be dissolved/precipitated or a material in/from which metal ions can be inserted/extracted, whereby the negative electrode active material layer 105 can be formed in a manner similar to that of the positive electrode active material layer 102. Note that the above-described material can be used as the conduction auxiliary agent and the binder.

In this embodiment, a lithium foil is used for the negative electrode 106. Since the ionic liquid according to an embodiment of the present invention has excellent reduction resistance and is stable to lithium in the negative-electrode material that has the lowest potential, with the use of the ionic liquid for an electrolyte solution, a power storage device having a high energy density and high reliability can be manufactured.

The electrolyte solution 108 and the electrolyte solution with which the separator 107 is impregnated may be made by mixing any of the ionic liquids in Embodiment 1 and electrolyte salt including a metal ion. In this embodiment, $Li(CF_3SO_2)_2N$ is used as the electrolyte salt including lithium.

The ionic liquid according to an embodiment of the present invention has a wide oxidation-reduction potential window, and thus is stable to a positive-electrode material and a negative-electrode material. Accordingly, the ionic liquid according to an embodiment of the present invention is used for the electrolyte solution 108 and the electrolyte solution with which the separator 107 is impregnated, whereby the reliability of the power storage device can be improved.

Next, the separator 107 is provided between the positive electrode 103 and the negative electrode 106 in the housing 109, and the housing 109 is filled with the electrolyte solution 108, whereby the power storage device 100 can be manufactured. Furthermore, the separator 107 impregnated with an electrolyte solution is provided between the positive electrode 103 and the negative electrode 106 in the housing 109, whereby the power storage device 110 can be manufactured.

Next, an example of a laminated power storage device is described with reference to FIG. 2A.

Figure 2A:
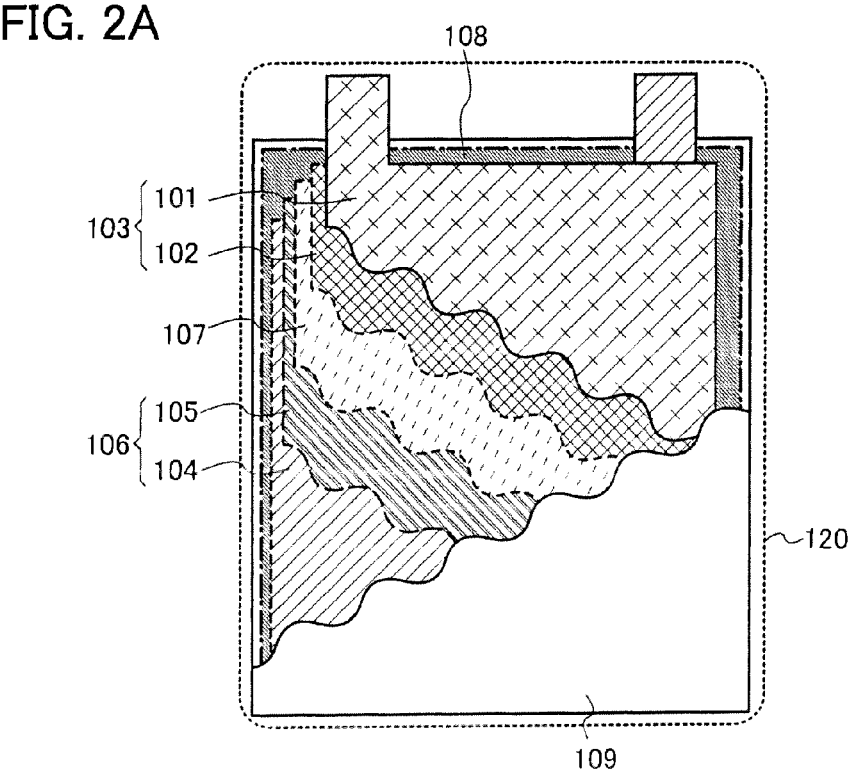
FIGS. 2A and 2B are a top view and a perspective view illustrating power storage devices.

A laminated power storage device 120 illustrated in FIG. 2A includes a positive electrode 103 including a positive electrode current collector 101 and a positive electrode active material layer 102, a negative electrode 106 including a negative electrode current collector 104 and a negative electrode active material layer 105, a separator 107, an electrolyte solution 108, and a housing 109. The separator 107 is placed between the positive electrode 103 and the negative electrode 106 provided in the housing 109. The inside of the housing 109 is filled with the electrolyte solution 108.

In the power storage device 120 illustrated in FIG. 2A, the positive electrode current collector 101 and the negative electrode current collector 104 also function as terminals for electrical contact with the outside. For this reason, each of the positive electrode current collector 101 and the negative electrode current collector 104 is provided to be partly exposed outside the housing 109.

For the housing 109 in the laminated power storage device 120, a laminate film, a polymer film, a metal film, or the like is preferably used.

Next, an example of a coin-type power storage device is described with reference to FIG. 2B.

Figure 2B:
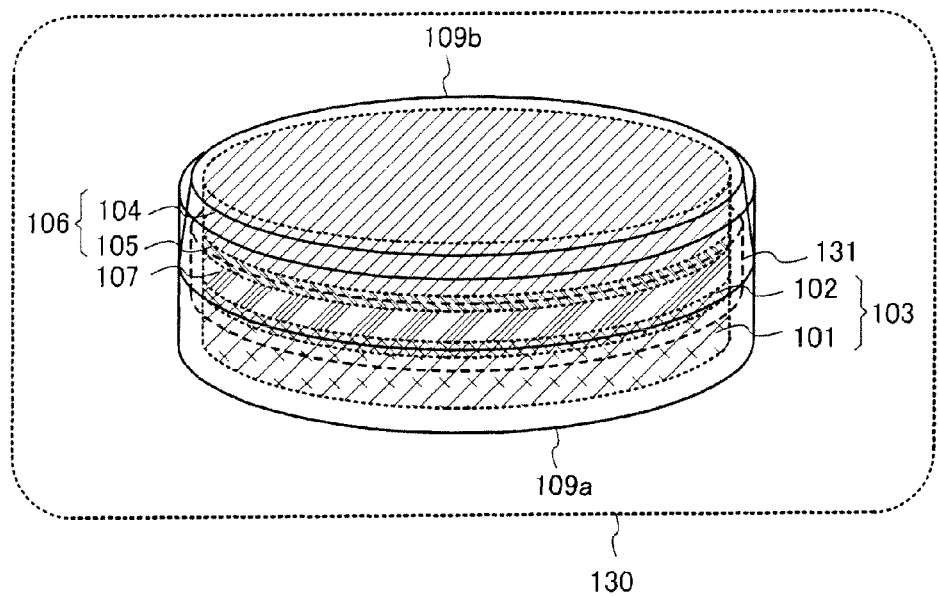

A coin-type power storage device 130 illustrated in FIG. 2B includes a positive electrode 103 including a positive electrode current collector 101 and a positive electrode active material layer 102, a negative electrode 106 including a negative electrode current collector 104 and a negative electrode active material layer 105, a separator 107, an electrolyte solution 108, and a housing 109, which is the same as the power storage device 100 illustrated in FIG. 1A. The housing in the power storage device 130 illustrated in FIG. 2B includes a first housing 109a and a second housing 109b. In the first housing 109a and the second housing 109b, the separator 107 impregnated with the electrolyte solution 108 is provided between the positive electrode 103 and the negative electrode 106.

Figure 3A:
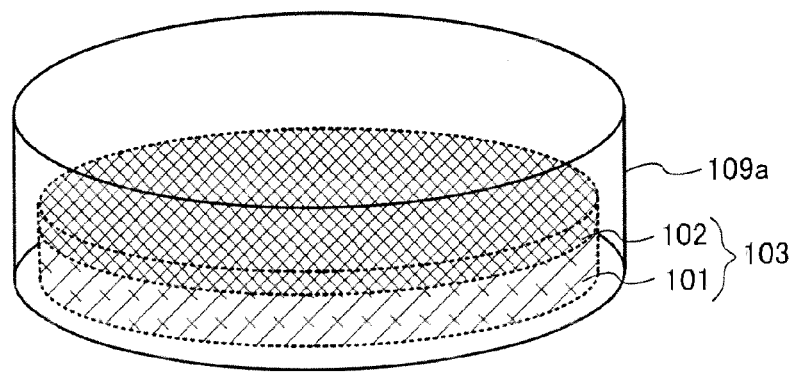
FIGS. 3A and 3B are perspective views illustrating a method for manufacturing a power storage device.

Next, an example of a method for manufacturing the power storage device 130 is described with reference to FIGS. 3A and 3B and FIG. 4.

First, the first housing 109a is prepared. The first housing 109a has a cylinder shape without one bottom surface. A material for the first housing 109a is preferably a conductive material for electrically connecting the positive electrode 103 to the outside. The first housing 109a may be formed with, for example, a metal material. In the first housing 109a, the positive electrode 103 including the positive electrode current collector 101 and the positive electrode active material layer 102 is provided (see FIG. 3A).

On the other hand, the second housing 109b is prepared. The second housing 109b has a truncated conical shape without a bottom surface having a smaller area than the other bottom surface. A material for the second housing 109b is preferably a conductive material for electrically connecting the negative electrode 106 to the outside. The second housing 109b may be formed with, for example, a metal material. In the second housing 109b, the negative electrode 106 including the negative electrode current collector 104 and the negative electrode active material layer 105 is provided (see FIG. 3B).

Figure 4:
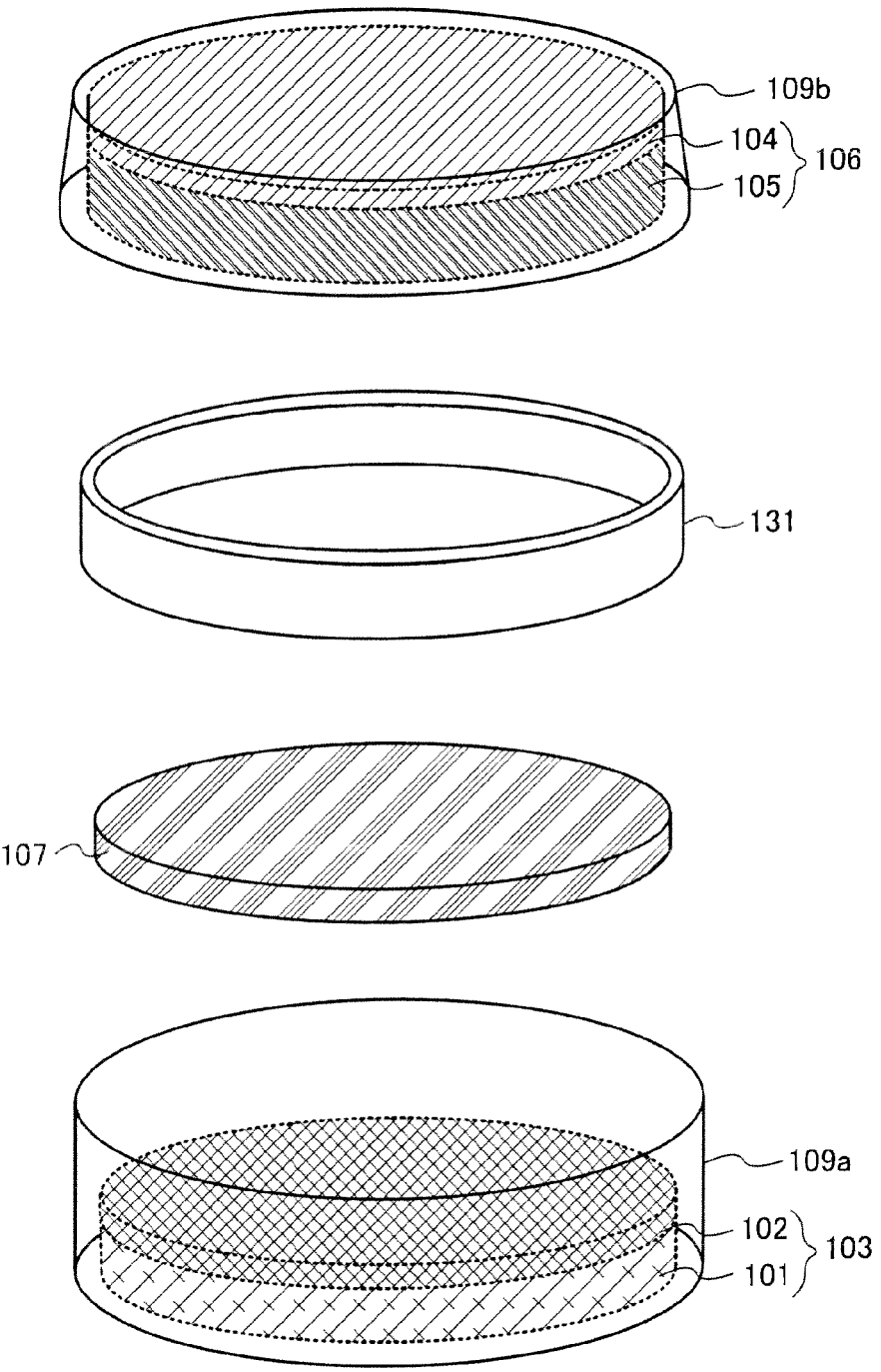
FIG. 4 is a perspective view illustrating a method for manufacturing a power storage device.

FIG. 4 illustrates the first housing 109a provided with the positive electrode 103 including the positive electrode current collector 101 and the positive electrode active material layer 102; a ring-shaped insulator 131; the separator 107 impregnated with an electrolyte solution; and the second housing 109b provided with the negative electrode 106 including the negative electrode current collector 104 and the negative electrode active material layer 105.

The ring-shaped insulator 131 is provided to surround the side of the positive electrode 103 provided in the first housing 109a. The ring-shaped insulator 131 has a function of insulating the positive electrode 103 from the negative electrode 106. The ring-shaped insulator 131 is preferably formed with the use of an insulating resin.

Figure 3B:
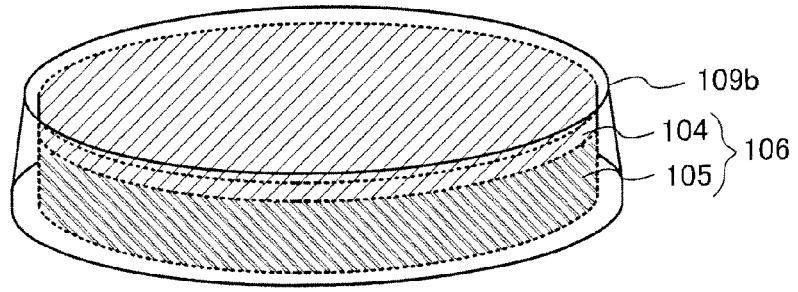

The second housing 109b provided with the negative electrode 106, which is illustrated in FIG. 3B, is put in the first housing 109a provided with the ring-shaped insulator 131. The separator 107 impregnated with an electrolyte solution is provided between the first housing 109a and the second housing 109b. The second housing 109b can be fit in the first housing 109a because the diameter of the second housing 109b is smaller than the diameter of the bottom surface of the first housing 109a. Since the positive electrode 103 and the negative electrode 106 are insulated from each other with the ring-shaped insulator 131, short circuit therebetween does not occur.

Through the above steps, the coin-type power storage device 130 illustrated in FIG. 2B can be manufactured.

The ionic liquid according to an embodiment of the present invention has a wide potential window and high electrochemical stability, and thus is stable to the selected positive-electrode material and negative-electrode material. Therefore, with the use of the ionic liquid according to an embodiment of the present invention for an electrolyte solution of a lithium-ion secondary battery, the reliability of the lithium-ion secondary battery can be increased.

The ionic liquid according to an embodiment of the present invention has a feature of a low melting point. With the use of the ionic liquid according to an embodiment of the present invention for an electrolyte solution of a lithium-ion secondary battery, the lithium-ion secondary battery can be operated in a low-temperature environment, i.e., the operating temperature can be widened.

Although the structures of the lithium-ion secondary battery and the manufacturing methods thereof are described with reference to FIGS. 1A and 1B, FIGS. 2A and 2B, FIGS. 3A and 3B, and FIG. 4, the power storage device according to an embodiment of the present invention is not limited thereto. As another example of the power storage device according to an embodiment of the present invention, a capacitor is given. Examples of the capacitor include a lithium-ion capacitor and an electric double layer capacitor.

In the case where the power storage devices 100, 110, 120, and 130 are used as lithium-ion capacitors, a material in/from which lithium ions and/or anions can be reversibly inserted/extracted may be used for the positive electrode active material layer 102. For the positive electrode active material layer 102 and the negative electrode active material layer 105, for example, active carbon, graphite, a conductive polymer, or a polyacene organic semiconductor (PAS) can be used.

The ionic liquid according to an embodiment of the present invention has a wide potential window and high electrochemical stability, and thus is stable to the selected positive-electrode material and negative-electrode material. Therefore, with the use of the ionic liquid according to an embodiment of the present invention for an electrolyte solution of a lithium-ion capacitor, the reliability of the lithium-ion capacitor can be increased.

The ionic liquid according to an embodiment of the present invention has a feature of a low melting point. With the use of the ionic liquid according to an embodiment of the present invention for an electrolyte solution of a lithium-ion capacitor, the lithium-ion capacitor can be operated in a low-temperature environment, i.e., the operating temperature can be widened.

In the case where the power storage devices 100, 110, 120, and 130 are used as electric double layer capacitors, for the positive electrode active material layer 102 and the negative electrode active material layer 105, for example, active carbon, a conductive polymer, or a polyacene organic semiconductor (PAS) can be used.

In the case where the power storage devices 100, 110, 120, and 130 are used as electric double layer capacitors, only a nonaqueous solvent can be used for the electrolyte solution 108 without use of electrolyte salt. For the nonaqueous solvent, one or more of the ionic liquids each according to an embodiment of the present invention can be used.

The ionic liquid according to an embodiment of the present invention has a wide potential window and high electrochemical stability, and thus is stable to the selected positive-electrode material and negative-electrode material. Therefore, with the use of the ionic liquid according to an embodiment of the present invention for an electrolyte solution of an electric double layer capacitor, the reliability of the electric double layer capacitor can be increased.

The ionic liquid according to an embodiment of the present invention has a feature of a low melting point. With the use of the ionic liquid according to an embodiment of the present invention for an electrolyte solution of an electric double layer capacitor, the electric double layer capacitor can be operated in a low-temperature environment, i.e., the operating temperature can be widened.

Although examples of a laminated power storage device and a coin-type power storage device are described in this embodiment, the power storage device according to an embodiment of the present invention is not limited thereto.

Various structures can be employed for the power storage device; for example, a stack type power storage device or a cylinder-type power storage device can be manufactured.

This embodiment can be implemented in appropriate combination with any of the structures described in the other embodiments.

Embodiment 3

In this embodiment, application of the power storage device according to an embodiment of the present invention is described.

The power storage device according to an embodiment of the present invention can be provided in a variety of electronic devices. Examples of the electronic devices include cameras such as digital cameras or video cameras, mobile phones, portable information terminals, e-book terminals, portable game machines, digital photo frames, and audio reproducing devices. Moreover, the power storage device according to an embodiment of the present invention can be provided in electrically propelled vehicles such as electric vehicles, hybrid vehicles, electric railway cars, working vehicles, carts, wheelchairs, and bicycles.

An electrolyte solution of a power storage device according to an embodiment of the present invention includes an ionic liquid according to an embodiment of the present invention. The ionic liquid according to an embodiment of the present invention has a wide potential window and high electrochemical stability, and thus is stable to the selected positive-electrode material and negative-electrode material. Therefore, with the use of the ionic liquid according to an embodiment of the present invention for an electrolyte solution of a power storage device, the reliability of the power storage device can be increased.

The ionic liquid according to an embodiment of the present invention has a feature of a low melting point. With the use of the ionic liquid according to an embodiment of the present invention for an electrolyte solution of a lithium-ion secondary battery, the lithium-ion secondary battery can be operated in a low-temperature environment, i.e., the operating temperature can be widened.

Figure 5A:
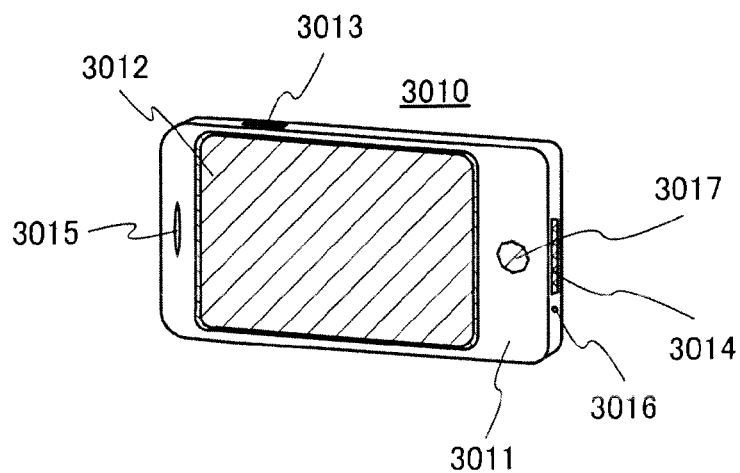
FIGS. 5A and 5B illustrate application examples of a power storage device.

FIG. 5A illustrates an example of a mobile phone. In a mobile phone 3010, a display portion 3012 is incorporated in a housing 3011. The housing 3011 is provided with an operation button 3013, an operation button 3017, an external connection port 3014, a speaker 3015, a microphone 3016, and the like. The power storage device according to an embodiment of the present invention is provided in such a mobile phone, whereby the reliability can be improved and the operating temperature can be widened. Note that as the power storage device, any one of a lithium-ion secondary battery, a lithium-ion capacitor, and an electric double layer capacitor or a combination thereof can be used.

Figure 5B:
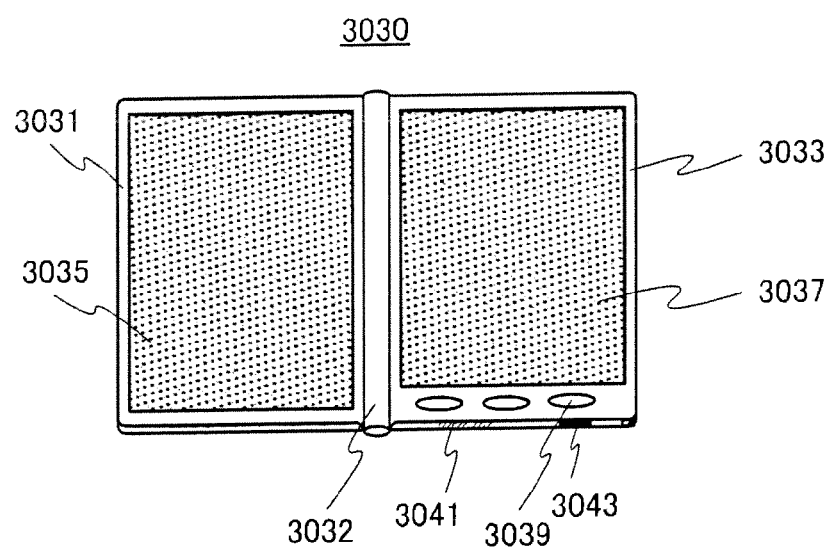

FIG. 5B illustrates an example of an e-book terminal. An e-book terminal 3030 includes two housings, a first housing 3031 and a second housing 3033, which are combined with each other with a hinge 3032. The first housing 3031 and the second housing 3033 can be opened and closed with the hinge 3032 as an axis. A first display portion 3035 and a second display portion 3037 are incorporated in the first housing 3031 and the second housing 3033, respectively. In addition, the second housing 3033 is provided with an operation button 3039, a power switch 3043, a speaker 3041, and the like. The power storage device according to an embodiment of the present invention is provided in such an e-book terminal, whereby the reliability can be improved and the operating temperature can be widened. Note that as the power storage device, any one of a lithium-ion secondary battery, a lithium-ion capacitor, and an electric double layer capacitor or a combination thereof can be used.

Figure 6A:
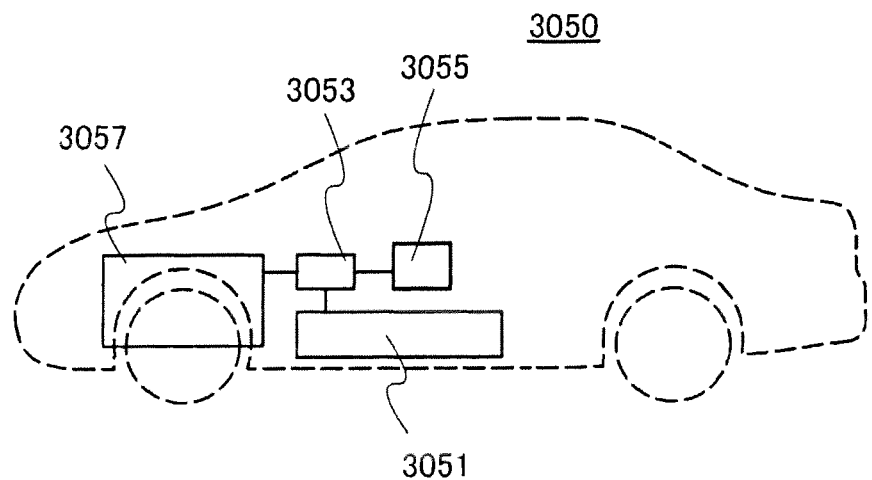
FIGS. 6A and 6B illustrate application examples of a power storage device.

FIG. 6A illustrates an example of an electric vehicle. An electric vehicle 3050 is equipped with a power storage device 3051. The output of the electric power of the power storage device 3051 is controlled by a control circuit 3053 and the electric power is supplied to a driving device 3057. The control circuit 3053 is controlled by a computer 3055.

The driving device 3057 includes a DC motor or an AC motor either alone or in combination with an internal-combustion engine. The computer 3055 outputs a control signal to the control circuit 3053 on the basis of an input data such as data of a driver's operation (e.g., acceleration, deceleration, or stop) or data during driving (e.g., data of an upgrade or a downgrade or data of a load on a driving wheel) of the electric vehicle 3050. The control circuit 3053 adjusts the electric energy supplied from the power storage device 3051 in accordance with the control signal of the computer 3055 to control the output of the driving device 3057. In the case where the AC motor is mounted, an inverter which converts direct current into alternate current is incorporated.

Note that as the power storage device 3051, any one of a lithium-ion secondary battery, a lithium-ion capacitor, and an electric double layer capacitor or a combination thereof can be used. The power storage device 3051 can be charged by external electric power supply using a plug-in technique. The power storage device according to an embodiment of the present invention is provided in the electric vehicle, whereby a charging time can be shortened and the convenience can be improved. Furthermore, the reliability can be increased and the operating temperature can be widened.

Figure 6B:
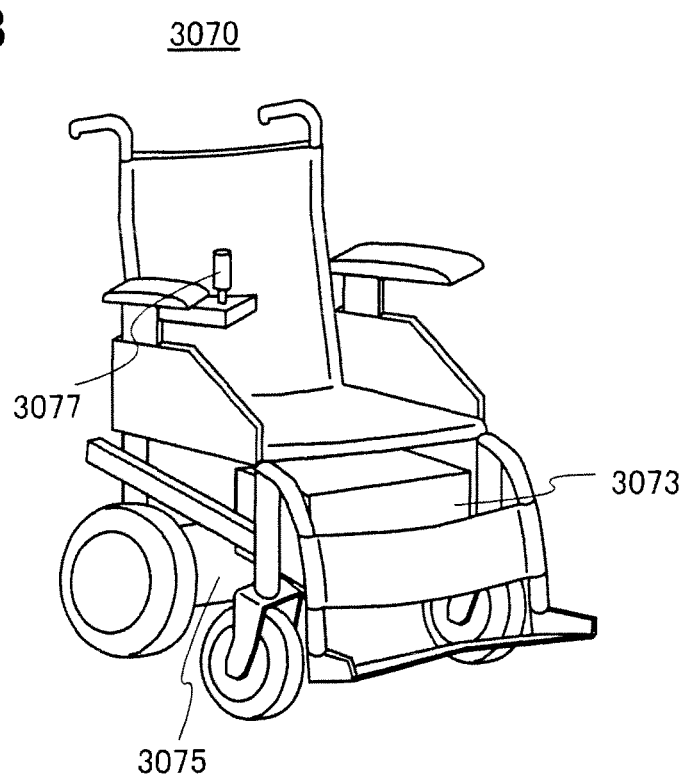

FIG. 6B illustrates an example of an electric wheelchair. A wheelchair 3070 includes a control portion 3073 provided with a power storage device, a power controller, a control means, and the like. The electric power of the power storage device is controlled by the control portion 3073 to be output and is supplied to a driving portion 3075. The control portion 3073 is connected to a controller 3077. By operation of the controller 3077, the driving portion 3075 can be driven via the control portion 3073 and speed and movement of the wheelchair 3070 such as moving forward/backward and a turn can be controlled.

As the power storage device, any one of a lithium-ion secondary battery, a lithium-ion capacitor, and an electric double layer capacitor or a combination thereof can be used. The power storage device can be charged by external electric power supply using a plug-in technique. When the power storage device according to an embodiment of the present invention is provided in the wheelchair 3070, a charging time can be shortened and the convenience can be improved. Furthermore, the reliability can be increased and the operating temperature can be widened.

Note that in the case where the power storage device is provided in electric railway cars as electrically propelled vehicles, the power storage device can be charged by power supply from overhead wires or conductive rails.

This embodiment can be combined with any of the structures described in the other embodiments or examples as appropriate.

Example 1

In this example, a method for producing 1,3-dimethyl-1-propylpyrrolidinium bis(trifluoromethanesulfonyl)amide (abbreviation: 3mP13-TFSA) represented by the structural formula (200) is described.

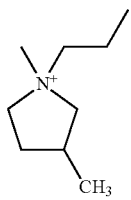 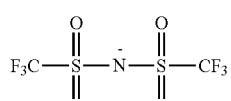

(200)

First, 4-amino-2-methyl-1-butanol (24.8 g, 240 mmol) and carbon tetrachloride (111 g, 720 mmol) were mixed under a nitrogen atmosphere at room temperature. Into this mixture, triphenylphosphine (69.2 g, 264 mmol) dissolved in dehydrated dichloromethane (150 ml) was added. Stirring was performed at 40° C. for 1 to 1.5 hours, and then pure water (50 ml) was added to the reacted solution and stirred well. Subsequently, an aqueous phase and a dichloromethane phase were separated. A yellow oily substance was extracted from the dichloromethane phase using pure water (50 ml×2 times). Then, the aqueous phase was washed with toluene (50 ml×3 times), and the solvent was removed by evaporation under reduced pressure to give a yellow oily substance.

Sodium hydroxide (19.2 g, 480 mmol) was dissolved in pure water (20 ml), and the sodium hydroxide solution was gradually added to the obtained yellow oily substance, and the mixture was stirred for 12 hours. After that, distillation was performed to give 3-methylpyrrolidine (18.7 g, 219 mmol) which is a colorless transparent liquid.

Into formic acid (21.6 g, 470 mmol) being water-cooled, 3-methylpyrrolidine (18.7 g, 219 mmol) was gradually added. Next, a 37% formaldehyde solution (26 ml, 330 mmol) was added to this solution. This solution was heated and refluxed at 100° C., was cooled back to room temperature after a bubble generation, and was stirred for about 30 minutes. Then, the solution was heated and refluxed again for one hour.

The formic acid was neutralized with sodium hydroxide, and then the target substance was extracted with diethyl ether and dried using magnesium sulfate, and the solvent was removed by evaporation. Then, distillation was performed, whereby 1,3-dimethylpyrrolidine (13.3 g, 134 mmol) which is a colorless transparent liquid was obtained.

Bromopropane (22.3 g, 182 mmol) was added to methylene chloride (10 ml) to which 1,3-dimethylpyrrolidine (12.0 g, 121 mmol) was added, and the mixture was heated and refluxed for 24 hours. The solvent was removed by evaporation, and the obtained white residue was recrystallized in ethanol and ethyl acetate and then dried under reduced pressure at 80° C. for 24 hours, whereby 1,3-dimethyl-1-propylpyrrolidinium bromide (13.9 g, 63.4 mmol) which is a white solid was obtained.

In pure water, 1,3-dimethyl-1-propylpyrrolidinium bromide (5.30 g, 23.9 mmol) and lithium bis(trifluoromethanesulfonyl)amide (7.55 g, 26.3 mmol) were mixed and stirred, so that an ionic liquid which is insoluble in water was obtained immediately. After that, the obtained ionic liquid was extracated with methylene chloride and then washed with pure water six times. The solvent was removed by evaporation and dried in vacuum at 100° C., so that 1,3-dimethyl-1-propylpyrrolidinium bis(trifluoromethanesulfonyl)amide (9.37 g, 22.2 mmol) was obtained.

The compound obtained through the above steps was identified as 1,3-dimethyl-1-propylpyrrolidinium bis(trifluoromethanesulfonyl)amide which is a target substance by using a nuclear magnetic resonance (NMR) and mass spectrometry.

$^1$H NMR data of the obtained compound is shown below.

$^1$H-NMR (CDCl$_3$, 400 MHz, 298 K): δ=0.97-1.05 (3H), 1.15-1.21 (3H), 1.67-1.99 (3H), 2.28-2.48 (1H), 2.58-2.78 (1H), 2.94-3.08 (1H), 3.06, 3.13 (3H), 3.18-3.34 (2H), 3.47-3.87 (3H)

Figure 7:
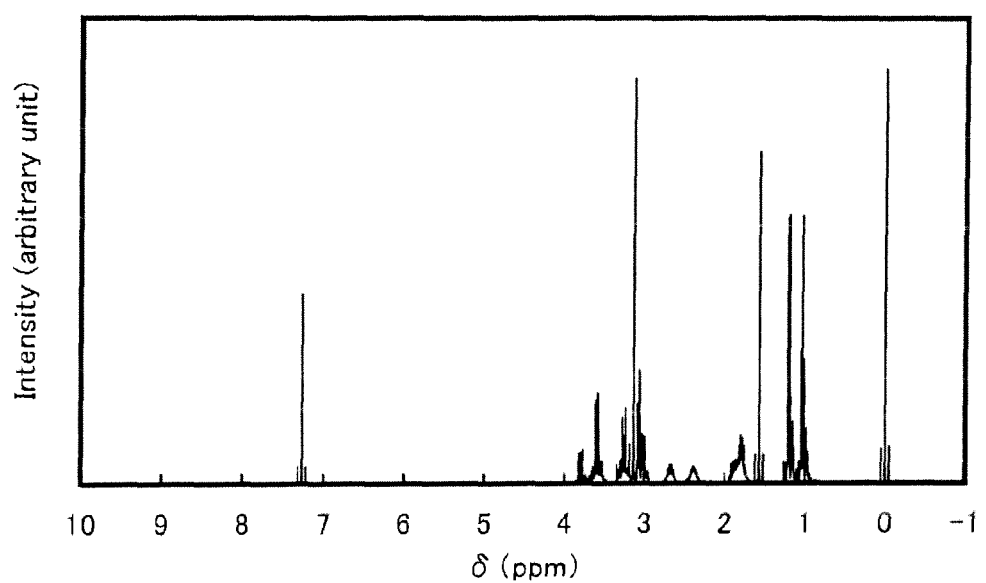
FIG. 7 is an NMR chart of 1,3-dimethyl-1-propylpyrrolidinium bis(trifluoromethanesulfonyl)amide (abbreviation: 3mP13-TFSA)

A $^1$H NMR chart of the obtained compound is shown in FIG. 7.

The measurement results of the electro spray ionization mass spectrometry (ESI-MS) of the obtained compound are shown below.

MS (ESI-MS): m/z=142.22 (M)$^+$; C$_9$H$_{20}$N (142.16), m/z=279.95 (M)$^-$; C$_2$F$_6$NO$_4$S$_2$ (279.92)

Next, physical property values of the obtained compound were obtained in the following manner.

The viscosity was measured with an oscillation type viscometer (VM-10A) produced by SEKONIC CORPORATION at 25° C. Since a measurement value obtained with the oscillation type viscometer is "viscosity (mPa·s)×density (g/ml)", the viscosity is obtained by dividing the measurement value by the density.

The conductivity was obtained by filling a conductivity cell, which is a housing made of a fluorine resin and includes a plate electrode produced by SUS Corporation, with a sample and by alternating current impedance measurement.

The alternating current impedance measurement uses impedance measurement system composed of a potentiostat and a frequency response analyzer (FRA) to analyze a response current against a small voltage amplitude applied to an object to be measured.

The alternating current impedance was measured with an electrochemical measurement system HZ-5000 produced by Hokuto Denko Corporation connected with a frequency response analyzer FRA5022 produced by NF Corporation, under the conditions that the AC (alternating current) amplitude was 10 mV and the temperature was 25° C.

The melting point was measured with a differential scanning calorimeter DSC200 produced by SII NanoTechnology Inc., under the conditions that the temperature range was from −100° C. to 100° C. and the temperature rising rate was 10° C./min.

The obtained compound had a viscosity of 68 mPa·s, a conductivity of 3.4 mS/cm, and a melting point of −14° C.

Example 2

In this example, a method for producing 1,3-dimethyl-1-propylpyrrolidinium bis(fluorosulfonyl)amide (abbreviation: 3mP13-FSA) represented by the structural formula (201) is described.

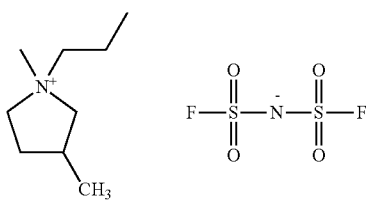

(201)

First, 1,3-dimethyl-1-propylpyrrolidinium bromide was synthesized in a manner similar to that in Example 1.

In pure water, 1,3-dimethyl-1-propylpyrrolidinium bromide (11.4 g, 51.3 mmol) and potassium bis(fluorosulfonyl) amide (12.3 g, 56.1 mmol) were mixed and stirred, so that an ionic liquid which is insoluble in water was obtained immediately. After that, the obtained ionic liquid was extracated with methylene chloride and then washed with pure water six times. The solvent was removed by evaporation and dried in vacuum at 100° C., so that 1,3-dimethyl-1-propylpyrrolidinium bis(fluorosulfonyl)amide (12.2 g, 37.8 mmol) was obtained.

The compound obtained through the above steps was identified as 1,3-dimethyl-1-propylpyrrolidinium bis(fluorosulfonyl)amide which is a target substance by using a nuclear magnetic resonance (NMR) and mass spectrometry.

$^1$H NMR data of the obtained compound is shown below.
$^1$H-NMR (CDCl$_3$, 400 MHz, 298 K): δ=0.99-1.08 (3H), 1.17-1.24 (3H), 1.74-1.97 (3H), 2.33-2.50 (1H), 2.60-2.78 (1H), 2.97-3.08 (1H), 3.09, 3.16 (3H), 3.20-3.37 (2H), 3.48-3.88 (3H)

Figure 8:
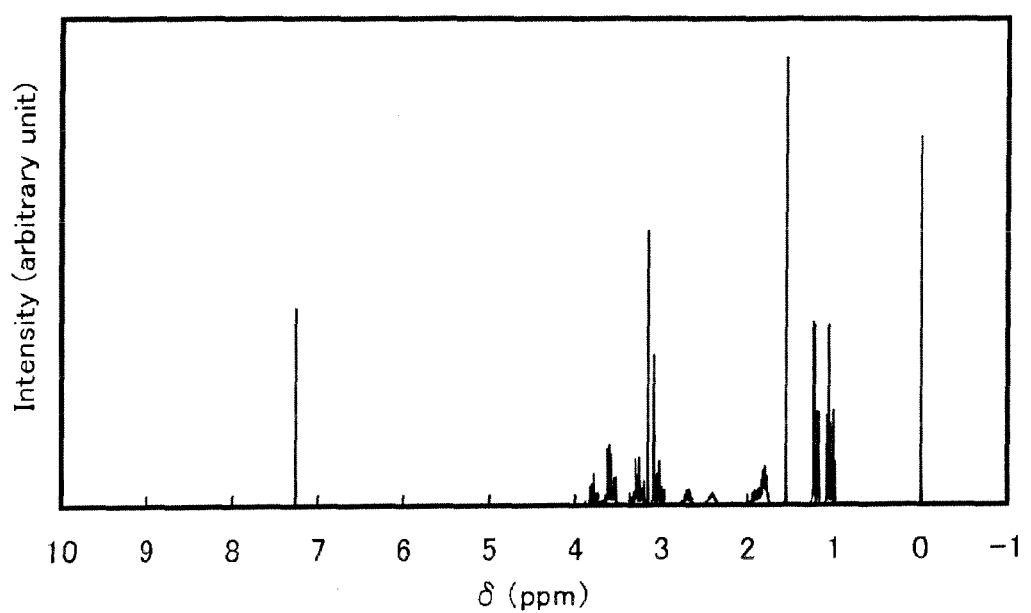
FIG. 8 is an NMR chart of 1,3-dimethyl-1-propylpyrrolidinium bis(fluorosulfonyl)amide (abbreviation: 3mP13-FSA)

A $^1$H NMR chart of the obtained compound is shown in FIG. 8.

The measurement results of the electron impact mass spectrometry (EI-MS) of the obtained compound are shown below
MS (EI-MS): m/z=142.23 (M)$^+$; C$_9$H$_{20}$N (142.16), m/z=180.00 (M)$^-$; F$_2$NO$_4$S$_2$ (179.92)

The physical property values of the obtained compound were obtained by a method similar to that in Example 1.

The obtained compound had a viscosity of 50 mPa·s, a conductivity of 6.4 mS/cm, a glass-transition temperature of −101° C., and no observed clear melting point.

Example 3

In this example, a method for producing 1,2-dimethyl-1-propylpyrrolidinium bis(fluorosulfonyl)amide (abbreviation: 2mP13-FSA) represented by the structural formula (202) is described.

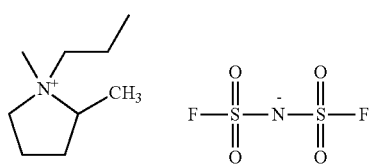

(202)

First, 2-methylpyrrolidine (8.52 g, 100 mmol) was gradually added to formic acid (12.8 g, 250 mmol) being water-cooled. Next, a 37% formaldehyde solution (11 ml, 150 mmol) was added to this solution. This solution was heated and refluxed at 100° C., was cooled back to room temperature after a bubble generation, and was stirred for about 30 minutes. Then, the solution was heated and refluxed again for one hour.

The formic acid was neutralized with sodium hydroxide, and then the target substance was extracted with dichloromethane and dried using magnesium sulfate, and the solvent was removed by evaporation. Then, distillation was performed, whereby 1,2-dimethylpyrrolidine (6.97 g, 70.3 mmol) which is a colorless transparent liquid was obtained.

Bromopropane (12.9 g, 105 mmol) was added to methylene chloride (10 ml) to which 1,2-dimethylpyrrolidine (6.97 g, 70.3 mmol) was added, and the mixture was heated and refluxed for 24 hours. The solvent was removed by evaporation, and the obtained white residue was recrystallized in ethanol and ethyl acetate and then dried under reduced pressure at 80° C. for 24 hours, whereby 1,2-dimethyl-1-propylpyrrolidinium bromide (8.36 g, 37.6 mmol) which is a white solid was obtained.

In pure water, 1,2-dimethyl-1-propylpyrrolidinium bromide (6.44 g, 29.0 mmol) and potassium bis(fluorosulfonyl) amide (6.99 g, 3.19 mmol) were mixed and stirred, so that an ionic liquid which is insoluble in water was obtained immediately. After that, the obtained ionic liquid was extracated with methylene chloride and then washed with pure water six times. The solvent was removed by evaporation and dried in vacuum at 100° C., so that 1,2-dimethyl-1-propylpyrrolidinium bis(fluorosulfonyl)amide (7.61 g, 23.6 mmol) was obtained.

The compound obtained through the above steps was identified as 1,2-dimethyl-1-propylpyrrolidinium bis(fluorosulfonyl)amide which is a target substance by using a nuclear magnetic resonance (NMR) and mass spectrometry.

$^1$H NMR data of the obtained compound is shown below.
$^1$H-NMR (CDCl$_3$, 400 MHz, 298 K): δ=1.05-1.11 (3H), 1.44-1.47 (3H), 1.75-1.96 (3H), 2.04-2.20 (1H), 2.22-2.35 (1H), 2.44-2.58 (1H), 2.81, 3.09 (3H), 2.94-3.89 (5H)

Figure 9:
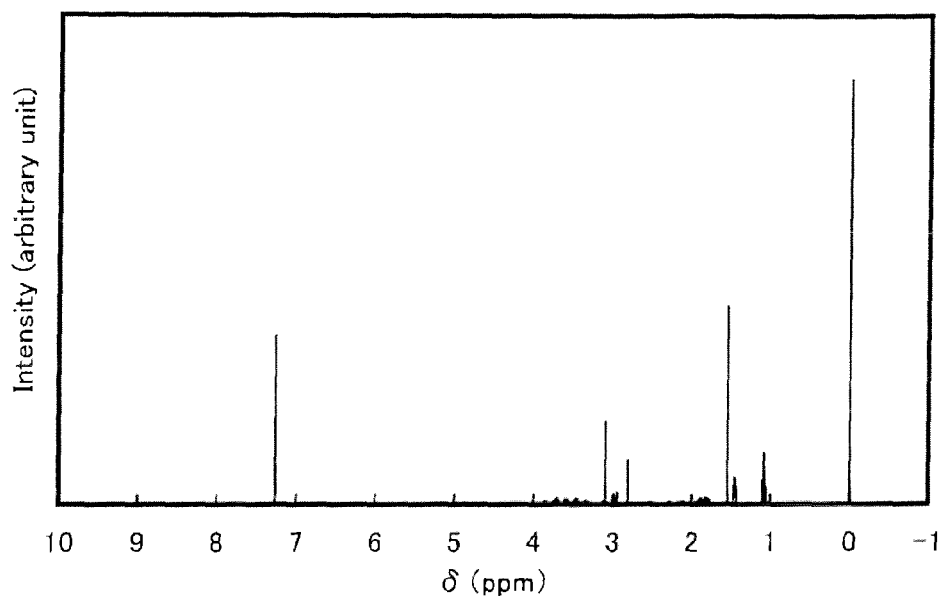
FIG. 9 is an NMR chart of 1,2-dimethyl-1-propylpyrrolidinium bis(fluorosulfonyl)amide (abbreviation: 2mP13-FSA)

A $^1$H NMR chart of the obtained compound is shown in FIG. 9.

The measurement results of the electron impact mass spectrometry (EI-MS) of the obtained compound are shown below.
MS (EI-MS): m/z=142.22 (M)$^+$; C$_9$H$_{20}$N (142.16), m/z=180.00 (M)$^-$; F$_2$NO$_4$S$_2$ (179.92)

The physical property values of the obtained compound were obtained by a method similar to that in Example 1.

The viscosity of the obtained compound was 82 mPa·s, and the conductivity thereof was 3.6 mS/cm. In addition, the melting point was −34° C.

Example 4

In this example, the calculation results of potential windows of 3mP13-TFSA in Example 1, 2mP13-FSA in Example 2, and 3mP13-FSA in Example 3 by linear sweep voltammetry are described.

Samples used in this example are described. As Sample 1, Sample 2, and Sample 3, 3mP13-TFSA in Example 1, 2mP13-FSA in Example 2, and 3mP13-FSA in Example 3 were used, respectively. Further, as Comparative Sample 1, 1-methyl-1-propylpyrrolidinium bis(fluorosulfonyl)amide (abbreviation: P13-FSA) produced by KANTO CHEMICAL CO., INC. was used, as Comparative Sample 2, 1-methyl-1-propylpyrrolidinium bis(trifluoromethanesulfonyl)amide (abbreviation: P13-TFSA) produced by Kishida Chemical Co., Ltd.) was used, and as Comparative Sample 3, 1-ethyl-3-methylimidazolium bis(fluorosulfonyl)amide (abbreviation: EMI-FSA) produced by KANTO CHEMICAL CO., INC. was used.

The measurement was performed with electrochemical measurement system HZ-5000 produced by HOKUTO DENKO CORPORATION in a glove box with an argon atmosphere. A glassy carbon electrode was used as a working electrode and a platinum wire was used for an opposite electrode. A silver wire immersed in a solution in which silver trifluoromethanesulfonate was dissolved in 1-ethyl-3-methylimidazolium bis(trifluoromethanesulfonyl)amide at a concentration of 0.1 M was used for a reference electrode. Oxidation-reduction potential of the ionic liquid was corrected with reference to the oxidation-reduction potential of ferrocene (Fc/Fc$^+$). The potential scanning speed was 50 mV/s.

Figure 10:
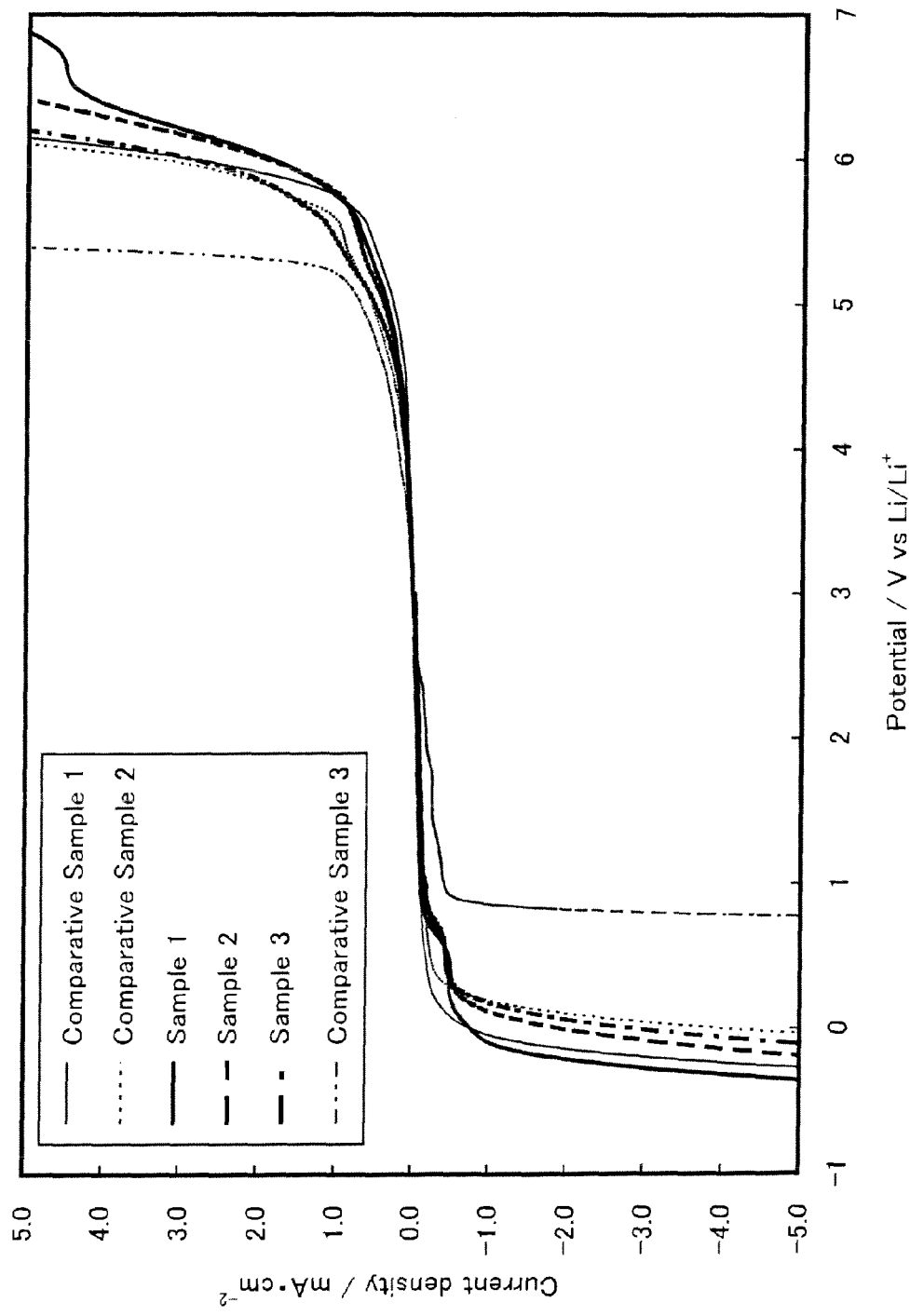
FIG. 10 shows linear sweep voltammograms of Samples 1 to 3 and Comparative Samples 1 to 3.

FIG. 10 shows linear sweep voltammograms of Samples 1 to 3 and Comparative Samples 1 to 3. In FIG. 10, the heavy lines indicate Samples 1 to 3 and the thin lines indicate Comparative Samples 1 to 3. The heavy solid line indicates Sample 1, the heavy dash line indicates Sample 2, and the heavy alternate long and short dash line indicates Sample 3. The thin solid line indicates Comparative Sample 1, the thin dotted line indicates Comparative Sample 2, and the thin alternate long and two short dashes line indicates Comparative Sample 3. Table 2 shows the reduction potentials, oxidation potentials, and potential windows of Samples 1 to 3 and Comparative Samples 1 to 3. A "potential window" in this example refers to a difference between an oxidation potential and a reduction potential. In FIG. 10, a potential at which an electric current density of −1 mA/cm$^2$ was detected during the scanning of potentials was calculated as a reduction potential. Further, in FIG. 10, a potential at which an electric current density of 1 mA/cm$^2$ was detected during the scanning of the potentials was calculated as an oxidation potential. The potential window was calculated by subtracting a "reduction potential" from an "oxidation potential".

TABLE 2

|  | Reduction [mA·cm$^{-2}$] | Oxidation [mA·cm$^{-2}$] | Potential window (v.s. Li/Li$^+$) [mA·cm$^{-2}$] |
|---|---|---|---|
| Sample 1 | −0.1 | 5.7 | 5.8 |
| Sample 2 | 0.1 | 5.8 | 5.7 |
| Sample 3 | 0.2 | 5.4 | 5.2 |
| Comparative Sample 1 | 0.2 | 5.6 | 5.4 |
| Comparative Sample 2 | 0.0 | 5.7 | 5.7 |
| Comparative Sample 3 | 0.9 | 5.2 | 4.3 |

Each of Samples 1 to 3, which is an ionic liquid according to an embodiment of the present invention, has a lower reduction potential and a higher oxidation potential than Comparative Sample 3 which is an ionic liquid including imidazolium-based cations. Furthermore, each of Samples 1 to 3, which is an ionic liquid according to an embodiment of the present invention, has a comparable potential window to Comparative Samples 1 and 2, each of which is an ionic liquid including cyclic quaternary ammonium-based cations.

Next, the measurement results of the solution resistances of the ionic liquids and the cell resistances of electric double layer capacitors each using an ionic liquid for an electrolyte solution are described with reference to FIG. 11 and FIGS. 12A and 12B.

First, a method for manufacturing the electric double layer capacitor is described with reference to FIG. 11.

Figure 11:
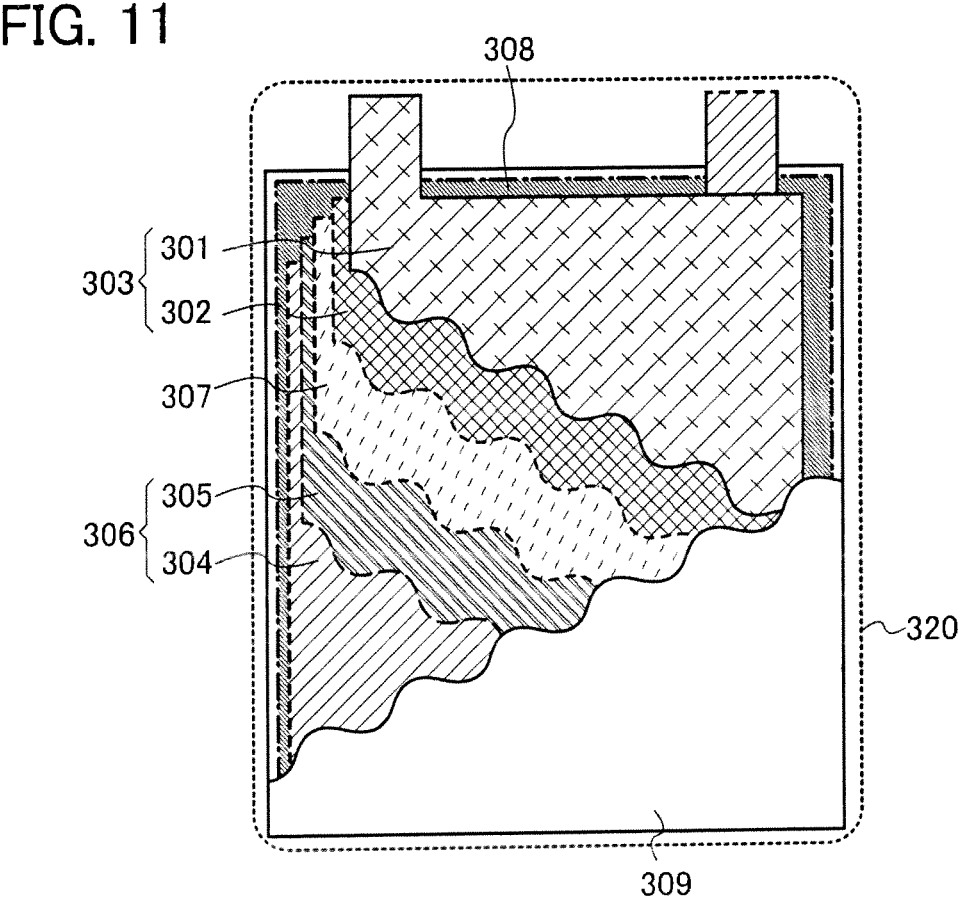
FIG. 11 is a top view illustrating an electric double layer capacitor.

The electric double layer capacitor manufactured in this example is a laminated electric double layer capacitor as illustrated in FIG. 11.

A laminated electric double layer capacitor 320 includes a positive electrode 303 including a positive electrode current collector 301 and a positive electrode active material layer 302, a negative electrode 306 including a negative electrode current collector 304 and a negative electrode active material layer 305, a separator 307, an electrolyte solution 308, and a housing 309.

A method for manufacturing the laminated electric double layer capacitor used in this example is described.

In this example, commercially available objects were used as the components except the electrolyte solution 308, i.e., the positive electrode 303, the negative electrode 306, the separator 307, and the housing 309. Specifically, an electrode sold by TAKUMI GIKEN CORPORATION was used as the positive electrode 303, in which aluminum foil was used for the positive electrode current collector 301, and active carbon/conductive material/styrene-butadiene rubber (SBR)/carboxy methyl cellulose (CMC) (=90/10/2/2) was used for the positive electrode active material layer 302. Similarly, an electrode sold by TAKUMI GIKEN CORPORATION was used as the negative electrode 306, in which aluminum foil was used for the negative electrode current collector 304, and active carbon/conductive material/SBR/CMC (=90/10/2/2) was used for the negative electrode active material layer 305. As the separator 307, solvent-spun regenerated cellulosic fiber (TF40) produced by NIPPON KODOSHI CORPORATION was used. As the housing 309, a valved body made of an aluminum laminated film produced by Hohsen Corp. (outer layer: a 25-μm-thick nylon/40-μm-thick aluminum layer, inner layer: a 22.5-μm-thick acid modified polypropylene/22.5-μm-polypropylene layer) was used. The separator 307 was interposed between the positive electrode 303 and the negative electrode 306, and they were put in the housing 309. The housing 309 was filled with the electrolyte solution 308 and then sealed.

Here, an electric double layer capacitor including 3mP13-FSA as the electrolyte solution 308 was used as Sample 4, and an electric double layer capacitor including P13-FSA produced by KANTO CHEMICAL CO., INC. as the electrolyte solution 308 was used as Comparative Sample 4.

Next, the solution resistances and the cell resistances of Sample 4 and Comparative Sample 4 were measured. The alternating current impedance measurement was performed for obtaining the solution resistances and the cell resistances.

The impedance of each electric double layer capacitor was measured while the temperatures of Sample 4 and Comparative Sample 4 are maintained at 25° C., 20° C., 10° C., 0° C., −10° C., −20° C. −30° C., and −40° C. in a thermostatic bath produced by ESPEC Corp. Here, an AC impedance measurement at constant potential was conducted with a multi-potentiostat VSP produced by by HOKUTO DENKO CORPORATION. The measurement conditions were as follows: the initial frequency was 200 kHz, AC amplitude was 10 mV. the last frequency was 20 mHz, and the measurement was performed after 15-minute application of a voltage of 1.25 V.

Figure 12A:
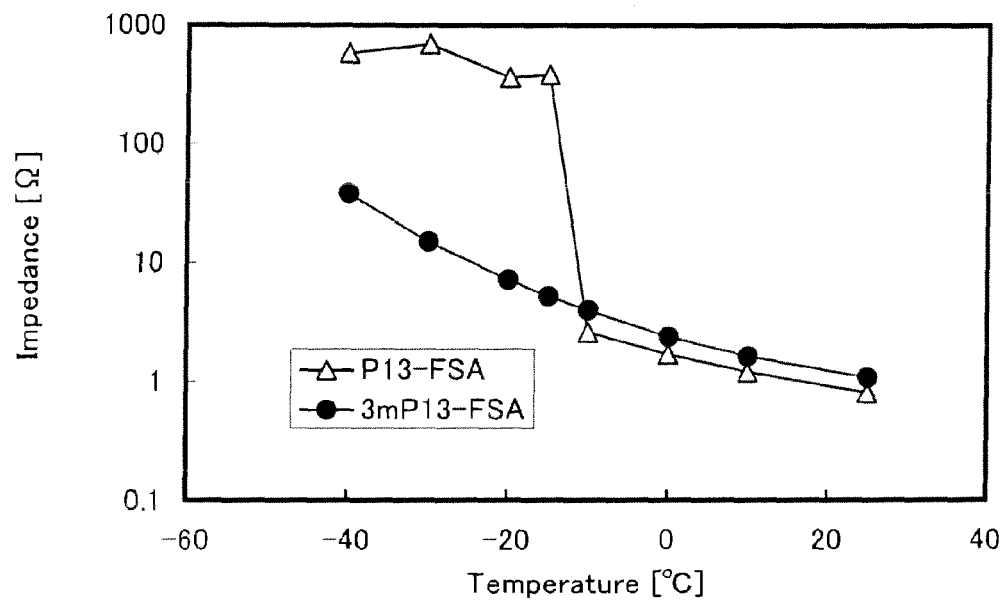
FIG. 12A is a graph showing the solution resistances of Sample 4 and Comparative Sample 4 and FIG. 12B is a graph showing the cell resistances thereof.
Figure 12B:
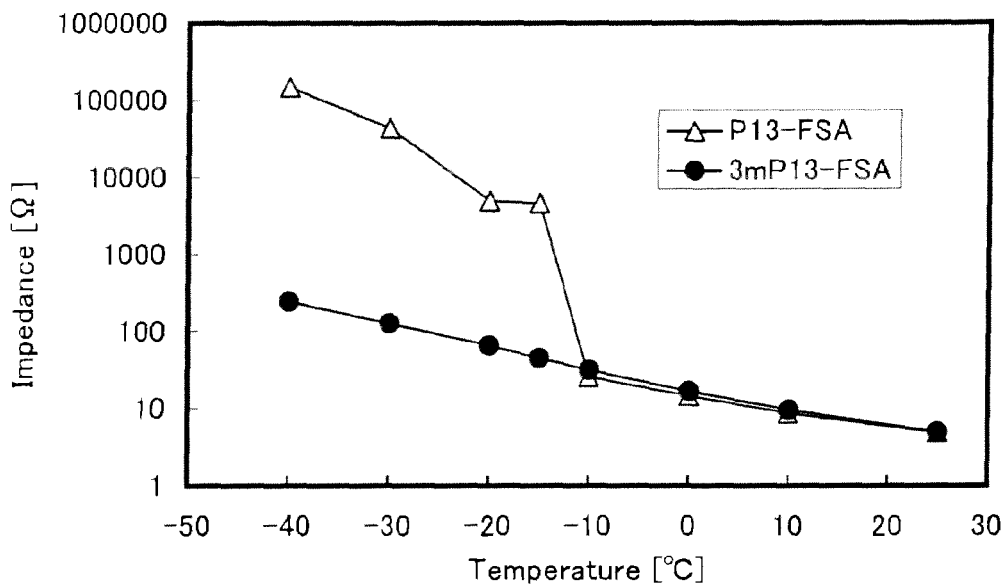

FIG. 12A shows the solution resistances of Sample 4 and Comparative Sample 4, and FIG. 12B shows the cell resistances of Sample 4 and Comparative Sample 4. Note that the solution resistances shown in FIG. 12A are obtained at a frequency of 200 kHz, and the cell resistances shown in FIG. 12B are obtained at a frequency of 20 mHz. In FIGS. 12A and 12B, the horizontal axis indicates temperature [° C.] and the vertical axis indicates impedance [Ω]. Also in FIGS. 12A and 12B, circles indicate Sample 4 and triangles indicate Comparative Sample 4.

As seen from FIGS. 12A and 12B, the resistance value of Comparative Sample 4 increases as the temperature is decreased, and the resistance value extremely increases when the temperature becomes −20° C. or lower. On the other hand, although the resistance value of Sample 4 also increases as the temperature is decreased, the resistance value does not extremely increases.

The reason of the extreme increase in resistance value is probably that phase transition from liquid to solid occurs in Comparative Sample 4 when the temperature becomes −20° C. or lower; whereas, liquid does not change to solid in Sample 4 as the temperature is decreased; thus, the resistance value did not increase extremely.

Next, the evaluation results of the load characteristics of an electric double layer capacitor using an ionic liquid for an electrolyte solution are described with reference to FIG. 13.

The laminated electric double layer capacitor illustrated in FIG. 11 was used for measuring the load characteristics.

Further, electric double layer capacitors having the same structure as Sample 4 and Comparative Sample 4 were fabricated. Here, an electric double layer capacitor having the same structure as Sample 4 was used as Sample 5, and an electric double layer capacitor having the same structure as Comparative Sample 4 was used as Comparative Sample 5. In addition, an electric double layer capacitor in which 1.0 M Et$_4$NBF$_4$/PC produced by Kishida Chemical Co., Ltd. is used as the electrolyte solution 308 was used as Comparative Sample 6. Note that Comparative Sample 6 has the same structure as the other electric double layer capacitors except for the electrolyte solution 308.

Next, Sample 5, Comparative Sample 5, and Comparative Sample 6 were subjected to a charge/discharge test. The charge/discharge test was performed with a battery charge/discharge tester HJ-1010D8 produced by HOKUTO DENKO CORPORATION at 25° C. The charging consisted of CC charging at 4 mA (10 C) followed by CV charging at 2.5 V (charge stop condition: 0.4 mA). The discharging was performed at 0.4 mA to 400 mA (1 C to 1000 C).

Figure 13:
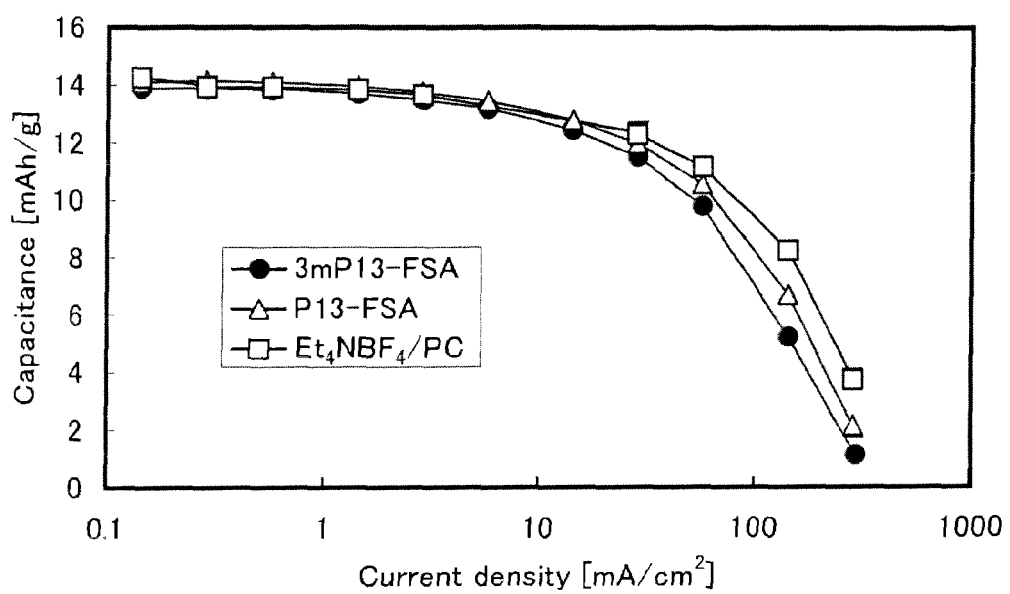
FIG. 13 is a graph showing output characteristics of Sample 5, Comparative Sample 5, and Comparative Sample 6.

FIG. 13 shows output characteristics of Sample 5, Comparative Sample 5, and Comparative Sample 6. The horizontal axis indicates current density and the vertical axis indicates capacitance. In FIG. 13, circles indicate Sample 5, triangles indicate Comparative Sample 5, and squares indicate Comparative Sample 6.

As shown in FIG. 13, it was found that Sample 5 using the ionic liquid according to an embodiment of the present invention for an electrolyte solution has comparable output characteristics to Comparative Sample 6 using an organic solvent for an electrolyte solution.

From the results shown in FIG. 10, FIG. 11, FIGS. 12A and 12B, and FIG. 13, the ionic liquid according to an embodiment of the present invention has a wide potential window, high electrochemical stability, and a low melting point.

Example 5

In this example, a method for producing 1-ethyl-1,3-dimethylpyrrolidinium bis(fluorosulfonyl)amide (abbreviation: 3mP12-FSA) represented by the structural formula (203) is described.

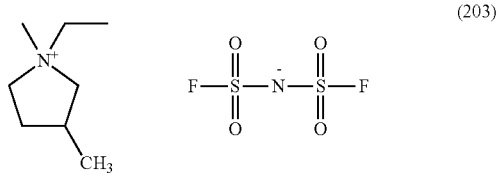

(203)

First, in an N$_2$ atmosphere, bromoethane (19.77 g, 182 mmol) was added to dehydrated tetrahydrofuran (10 ml) to which 1,3-dimethylpyrrolidine (12.0 g, 121 mmol) was added, and the mixture was heated and refluxed for 24 hours. Next, the solvent was removed by evaporation, and the obtained white residue was recrystallized in ethanol and ethyl acetate and then dried under reduced pressure at 80° C. for 24 hours, whereby 1-ethyl-1,3-dimethylpyrrolidinium bromide (12.90 g, 62 mmol) which is a white solid was obtained.

In pure water, 1-ethyl-1,3-dimethylpyrrolidinium bromide (12.90 g, 62 mmol) and potassium bis(fluorosulfonyl)amide (10.08 g, 46 mmol) were mixed and stirred, so that an ionic liquid which is insoluble in water was obtained immediately. After that, the obtained ionic liquid was extracated with methylene chloride and then washed with pure water six times. The solvent was removed by evaporation and dried under reduced pressure at 60° C. for approximately eight hours, so that 1-ethyl-1,3-dimethylpyrrolidinium bis(fluorosulfonyl)amide (16.26 g, 53 mmol) was obtained.

The compound obtained through the above steps was identified as 1-ethyl-1,3-dimethylpyrrolidinium bis(fluorosulfonyl)amide which is a target substance by using a nuclear magnetic resonance (NMR) and mass spectrometry.

$^1$H NMR data of the obtained compound is shown below.

$^1$H-NMR (CDCl$_3$, 400 MHz, 298 K): δ=1.15-1.25 (3H), 1.35-1.55 (3H), 1.83-1.89 (1H), 2.31-2.50 (1H), 2.58-2.78 (1H), 2.94-3.09 (1H), 2.99, 3.05, 3.09, 3.15 (3H), 3.31-3.62 (2H), 3.45-3.62 (2H), 3.62, 3.83 (1H)

Figure 14:
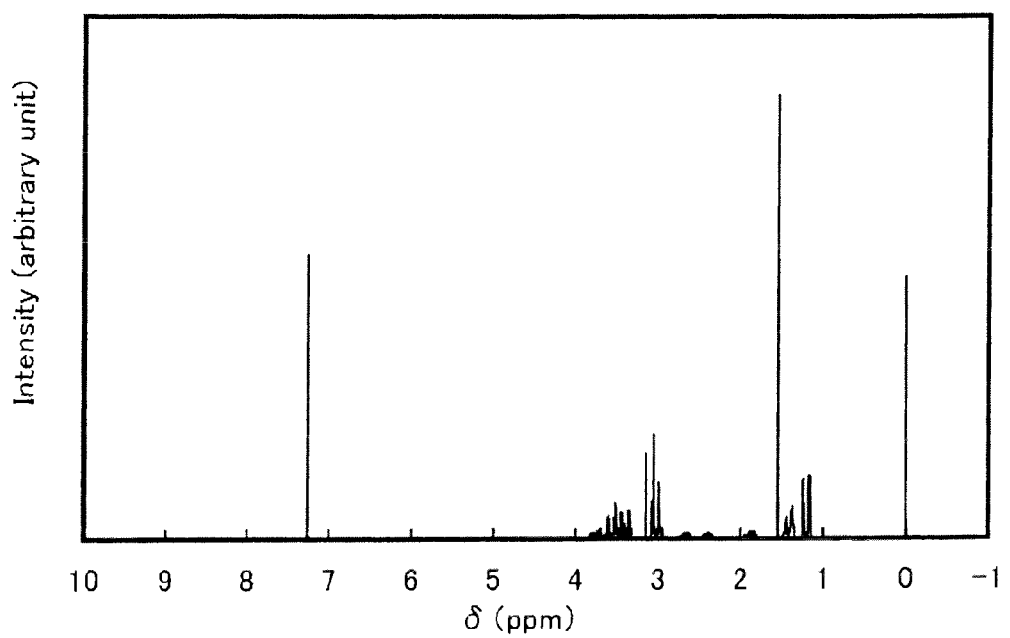
FIG. 14 is an NMR chart of 1-ethyl-1,3-dimethylpyrrolidinium bis(fluorosulfonyl)amide (abbreviation: 3mP12-FSA)

A $^1$H NMR chart of the obtained compound is shown in FIG. 14.

The measurement results of the electro spray ionization mass spectrometry (ESI-MS) of the obtained compound are shown below.

MS (ELMS): m/z=142.23 (M)$^+$; C$_9$H$_{20}$N (142.16), m/z=180.00 (M)$^-$; F$_2$NO$_4$S$_2$ (179.92)

The physical property values of the obtained compound were obtained by a method similar to that in Example 1.

The viscosity of the obtained compound was 42 mPa·s, and the conductivity thereof was 8.9 mS/cm. In addition, the melting point was −26° C.

Next, the calculation result of a potential window of 3mP12-FSA by linear sweep voltammetry is described.

The measurement was performed with electrochemical measurement system HZ-5000 produced by HOKUTO DENKO CORPORATION in a glove box with an argon atmosphere. A glassy carbon electrode was used as a working electrode and a platinum wire was used for an opposite electrode. A silver wire immersed in a solution in which silver trifluoromethanesulfonate was dissolved in 1-ethyl-3-methylimidazolium bis(trifluoromethanesulfonyl)amide at a concentration of 0.1 M was used for a reference electrode. Oxidation-reduction potential of the ionic liquid was corrected with reference to the oxidation-reduction potential of ferrocene (Li/Li$^+$). The potential scanning speed was 50 mV/s.

Figure 15:
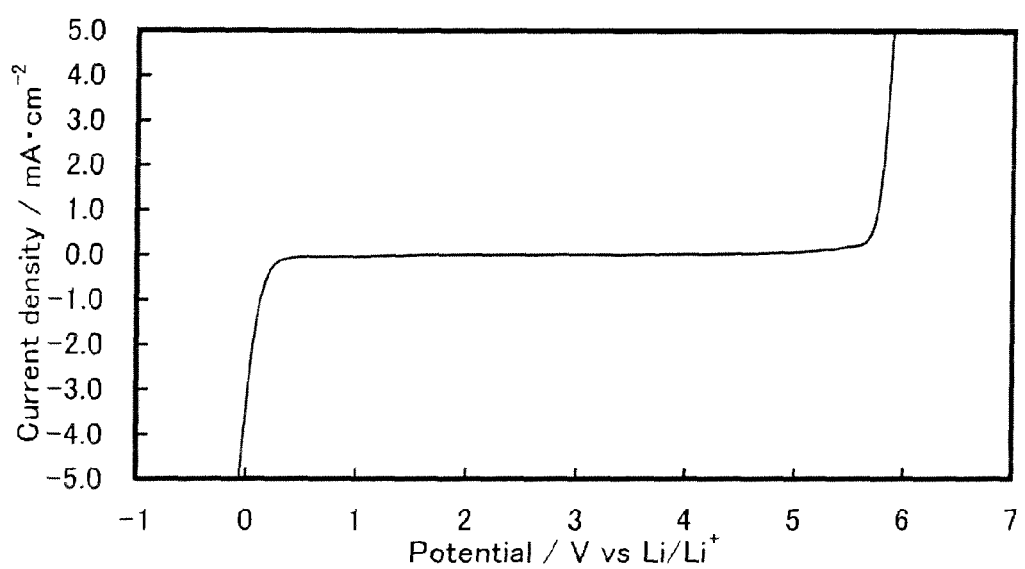
FIG. 15 shows a linear sweep voltammogram of 3mP12-FSA.

FIG. 15 shows a linear sweep voltammogram of 3mP12-FSA. In FIG. 15, a potential at which an electric current density of −1 mA/cm$^2$ was detected during the scanning of potentials was calculated as a reduction potential. Further, in FIG. 15, a potential at which an electric current density of 1 mA/cm$^2$ was detected during the scanning of the potentials was calculated as an oxidation potential. The potential window was calculated by subtracting a "reduction potential" from an "oxidation potential". From the results shown in FIG. 15, the reduction potential was 0.2 V, the oxidation potential was 5.6 V, and the potential window was 5.4 V. Consequently, 3mP12-FSA is an ionic liquid having a wide potential window.

Example 6

In this example, the results of a charge/discharge test of a lithium-ion secondary battery according to an embodiment of the present invention are described.

First, a method for manufacturing a lithium-ion secondary battery is described with reference to FIG. 16.

Figure 16:
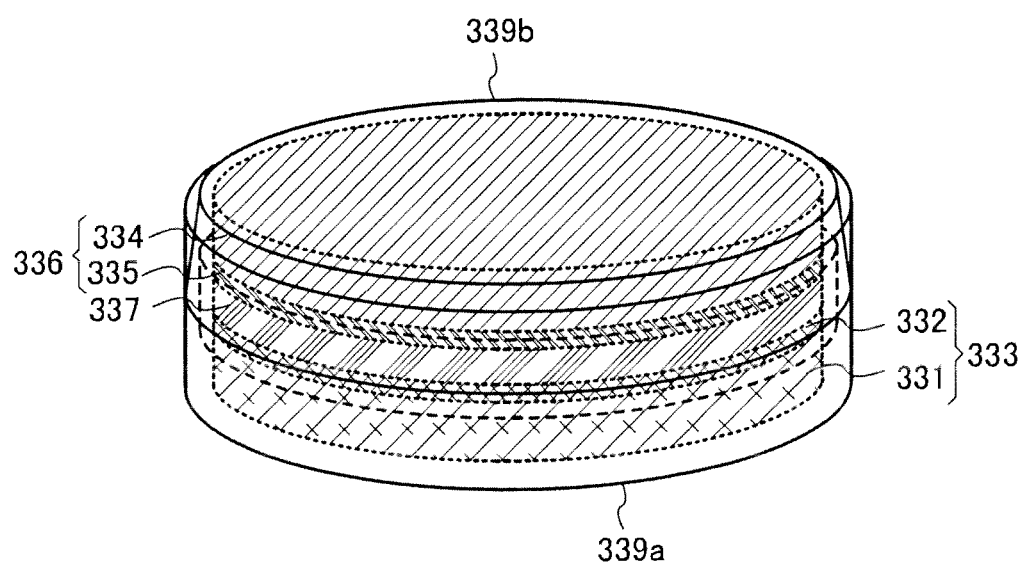
FIG. 16 is a perspective view illustrating a lithium-ion secondary battery.

The lithium-ion secondary battery manufactured in this example is a coin-type lithium-ion secondary battery as shown in FIG. 16.

A coin-type lithium-ion secondary battery 330 includes a positive electrode 333 including a positive electrode current collector 331 and a positive electrode active material layer 332, a negative electrode 336 including a negative electrode current collector 334 and a negative electrode active material layer 335, a separator 337, and housings 339$a$ and 339$b$.

A method for manufacturing the coin-type lithium-ion secondary battery in this example is described.

In this example, commercially available objects were used as the components except the electrolyte solution, i.e., the positive electrode 333, the negative electrode 336, the separator 337, and the housings 339a and 339b. Specifically, aluminum foil was used for the positive electrode current collector 331 and the positive electrode active material layer 332 including LiFePO$_4$/acetylene black/polyvinylidene difluoride (PVDF) (=85/7/8) was formed over the positive electrode current collector 331, so that the positive electrode 333 was formed. A lithium electrode was used as the negative electrode 336, and membrane filter (Durapore VVLP04700) produced by Merck Ltd., was used as the separator 337.

In addition, 2032 type coin cells sold by Hohsen Corp. were used as the housings 339a and 339b. The positive electrode 333 was put in the housing 339a, the electrolyte solution was injected into the housing, and the negative electrode 336 and the housing 339b were stacked thereover. The housing 339a and the housing 339b were pressed and crimped to each other with a "coin cell crimper"; thus, the coin-type lithium-ion secondary battery was manufactured.

Here, as Sample 6, a lithium-ion secondary battery for which an electrolyte solution obtained by dissolving lithium bis(trifluoromethanesulfonyl)amide (abbreviation: LiTFSA) of approximately 1 M in 3mP13-FSA is used was used; and as Sample 7, a lithium-ion secondary battery for which an electrolyte solution obtained by dissolving LiTFSA in 3mP12-FSA is used was used.

Sample 6 and Sample 7 were subjected to a charge/discharge test. The charge/discharge test was performed with a battery charge/discharge tester HJ-1010D8 produced by HOKUTO DENKO CORPORATION at −25° C. in a thermostatic bath produced by ESPEC Corp. The charging consisted of CC charging at 0.04 mA (0.02 C) to increase the voltage to 4.0 V. The discharging was performed at 0.04 mA to 0.2 mA (0.02 C to 0.1 C).

Figure 17A:
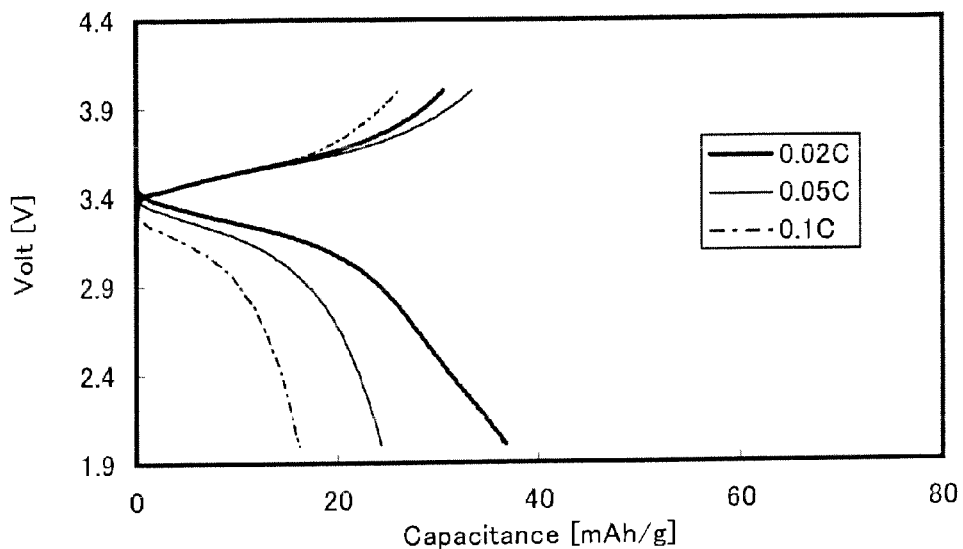
FIG. 17A is a graph showing output characteristics of Sample 6 and FIG. 17B is a graph showing output characteristics of Sample 7.
Figure 17B:
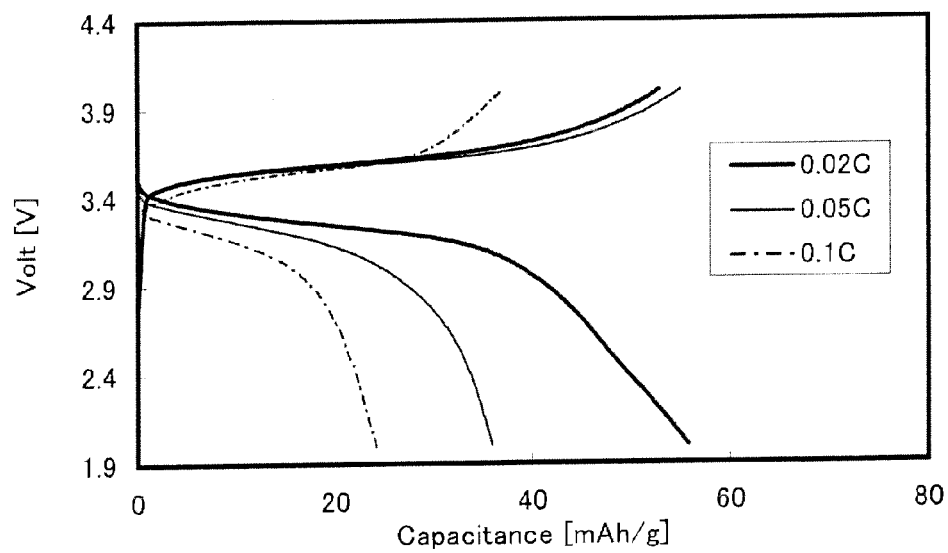

FIG. 17A shows output characteristics of Sample 6, and FIG. 17B shows output characteristics of Sample 7. The horizontal axis indicates capacitance and the vertical axis indicates voltage.

As shown in FIGS. 17A and 17B, each of Sample 6 and Sample 7 in which an electrolyte solution includes an ionic liquid according to an embodiment of the present invention, is a lithium-ion secondary battery which can be charged/discharged at a low-temperature environment of −25° C. Therefore, an ionic liquid according to an embodiment of the present invention does not change the phase from liquid to solid at a low-temperature environment of −25° C.

This application is based on Japanese Patent Application serial no. 2011-125116 filed with Japan Patent Office on Jun. 3, 2011, the entire contents of which are hereby incorporated by reference.

What is claimed is:

1. An ionic liquid represented by a general formula (G0),

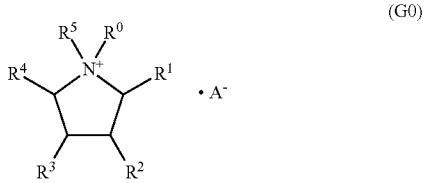

(G0)

wherein:
one of $R^0$ and $R^5$ is any of a methoxy group, a methoxymethyl group, and a methoxyethyl group;
the other of $R^0$ and $R^5$ is an alkyl group having 1 to 20 carbon atoms, or a hydrogen atom;
one or two of $R^1$ to $R^4$ are any of an alkyl group having 1 to 20 carbon atoms, a methoxy group, a methoxymethyl group, and a methoxyethyl group;
the others of $R^1$ to $R^4$ are each a hydrogen atom; and
$A^-$ is a univalent imide-based anion, a univalent methide-based anion, a perfluoroalkyl sulfonic acid anion, tetrafluoroborate, or hexafluorophosphate.

2. The ionic liquid according to claim 1, wherein $A^-$ is any one of univalent anions selected from $(C_nF_{2n+1}SO_2)_2N^-$ (n=0 to 4), $(C_mF_{2m+1}SO_3)-$ (m=0 to 4), and $CF_2(CF_2SO_2)_2N-$.

3. The ionic liquid according to claim 1, wherein the one or two of $R^1$ to $R^4$ are each an alkyl group having 1 to 4 carbon atoms.

4. The ionic liquid according to claim 1, wherein:
$R^1$ and $R^2$ are individually any of an alkyl group having 1 to 20 carbon atoms, a methoxy group, a methoxymethyl group, and a methoxyethyl group, and
$R^3$ and $R^4$ are each a hydrogen atom.

5. The ionic liquid according to claim 4, wherein $R^1$ and $R^2$ are individually an alkyl group having 1 to 4 carbon atoms.

6. The ionic liquid according to claim 1, wherein:
$R^1$ is any of an alkyl group having 1 to 20 carbon atoms, a methoxy group, a methoxymethyl group, and a methoxyethyl group, and
$R^2$ to $R^4$ are each a hydrogen atom.

7. The ionic liquid according to claim 1, wherein:
$R^2$ is any of an alkyl group having 1 to 20 carbon atoms, a methoxy group, a methoxymethyl group, and a methoxyethyl group, and
$R^1$, $R^3$ and $R^4$ are each a hydrogen atom.

8. A power storage device comprising a positive electrode, a negative electrode, a separator, and an electrolyte solution comprising an ionic liquid represented by a general formula (G0),

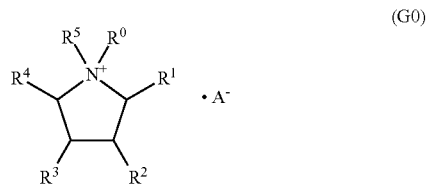

(G0)

wherein:
one of $R^0$ and $R^5$ is any of a methoxy group, a methoxymethyl group, and a methoxyethyl group;
the other of $R^0$ and $R^5$ is an alkyl group having 1 to 20 carbon atoms, or a hydrogen atom;
one or two of $R^1$ to $R^4$ are any of an alkyl group having 1 to 20 carbon atoms, a methoxy group, a methoxymethyl group, and a methoxyethyl group;
the others of $R^1$ to $R^4$ are each a hydrogen atom; and
$A^-$ is a univalent imide-based anion, a univalent methide-based anion, a perfluoroalkyl sulfonic acid anion, tetrafluoroborate, or hexafluorophosphate.

9. The power storage device according to claim 8, wherein $A^-$ is any one of univalent anions selected from $(C_nF_{2n+1}SO_2)_2N^-$ (n=0 to 4), $(C_mF_{2m+1}SO_3)-$ (m=0 to 4), and $CF_2(CF_2SO_2)_2N-$.

10. The power storage device according to claim 8, wherein the one or two of $R^1$ to $R^4$ are each an alkyl group having 1 to 4 carbon atoms.

11. The power storage device according to claim 8, wherein:
- $R^1$ and $R^2$ are individually any of an alkyl group having 1 to 20 carbon atoms, a methoxy group, a methoxymethyl group, and a methoxyethyl group, and
- $R^3$ and $R^4$ are each a hydrogen atom.

12. The power storage device according to claim 11, wherein $R^1$ and $R^2$ are individually an alkyl group having 1 to 4 carbon atoms.

13. The power storage device according to claim 8, wherein:
- $R^1$ is any of an alkyl group having 1 to 20 carbon atoms, a methoxy group, a methoxymethyl group, and a methoxyethyl group, and
- $R^2$ to $R^4$ are each a hydrogen atom.

14. The power storage device according to claim 8, wherein:
- $R^2$ is any of an alkyl group having 1 to 20 carbon atoms, a methoxy group, a methoxymethyl group, and a methoxyethyl group, and
- $R^1$, $R^3$ and $R^4$ are each a hydrogen atom.

15. The power storage device according to claim 8, wherein the electrolyte solution further comprises an electrolyte salt including a lithium ion.

16. The power storage device according to claim 8, wherein the power storage device is a lithium-ion capacitor or an electric double layer capacitor.

17. The power storage device according to claim 8, wherein the power storage device is a lithium-ion secondary battery.

* * * * *

UNITED STATES PATENT AND TRADEMARK OFFICE
CERTIFICATE OF CORRECTION

PATENT NO. : 9,171,677 B2
APPLICATION NO. : 14/600135
DATED : October 27, 2015
INVENTOR(S) : Kyosuke Ito et al.

Page 1 of 2

It is certified that error appears in the above-identified patent and that said Letters Patent is hereby corrected as shown below:

In the Specification:

Col. 6, line 8, "each alkyl" should read --each an alkyl--

Col. 9, line 39, "formula (100)." should read --formula (100),--

Col. 10, line 36, "Here." should read --Here,--

Col. 10, line 43, "is to 3s" should read --1s to 3s--

Col. 12, line 57, "hydride." should read --hydrido.--

Col. 12, line 58, "hydride" should read --hydrido--

Col. 13, line 38, "hydride." should read --hydrido.--

Col. 13, line 39, "hydride" should read --hydrido--

Col. 14, line 44, "example," should read --example.--

Col. 25, line 23, "below" should read --below.--

Col. 28, line 32, "20°C." should read -- -20° C.,--

Col. 28, line 37, "10 mV. the" should read --10 mV, the--

Col. 30, line 19, "MS (ELMS):" should read --MS (EI-MS):--

Signed and Sealed this
Third Day of May, 2016

Michelle K. Lee
*Director of the United States Patent and Trademark Office*

In the Claims:

Claim 2, Col. 32, line 14, "$(C_mF_{2m+1}SO_3)$ — (m=0 to 4), and $CF_2(CF_2SO_2)_2N$ —." should read --$(C_mF_{2m+1}SO_3)^-$ (m=0 to 4), and $CF_2(CF_2SO_2)_2 N^-$--

Claim 9, Col. 32, lines 63-64, "$(C_mF_{2m+1}SO_3)$ — (m=0 to 4), and $CF_2(CF_2SO_2)_2N$ —." should read --$(C_mF_{2m+1}SO_3)^-$ (m=0 to 4), and $CF_2(CF_2SO_2)_2 N^-$--